United States Patent
Hojeibane et al.

(10) Patent No.: US 7,351,256 B2
(45) Date of Patent: Apr. 1, 2008

(54) FRAME BASED UNIDIRECTIONAL FLOW PROSTHETIC IMPLANT

(75) Inventors: Hikmat Hojeibane, Princeton, NJ (US); David Christopher Majercak, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 125 days.

(21) Appl. No.: 10/402,180

(22) Filed: Mar. 28, 2003

(65) Prior Publication Data

US 2004/0093070 A1  May 13, 2004

Related U.S. Application Data

(60) Provisional application No. 60/379,604, filed on May 10, 2002.

(51) Int. Cl.
*A61F 2/06* (2006.01)
*A61F 2/24* (2006.01)

(52) U.S. Cl. ..................................... 623/1.24
(58) Field of Classification Search ............... 623/1.24, 623/1.26, 2.1–2.19, 900
See application file for complete search history.

(56) References Cited

U.S. PATENT DOCUMENTS

| | | |
|---|---|---|
| 4,323,525 A | 4/1982 | Bornat |
| 4,692,164 A | 9/1987 | Dzemeshkevich et al. |
| 4,725,274 A | 2/1988 | Lane et al. |
| 4,790,843 A | 12/1988 | Carpentier et al. |
| 4,892,541 A | 1/1990 | Alonso |
| 4,969,896 A | 11/1990 | Shors |
| 5,032,128 A | 7/1991 | Alonso |
| 5,037,434 A | 8/1991 | Lane |
| 5,123,919 A | 6/1992 | Sauter et al. |
| 5,147,391 A | 9/1992 | Lane |
| 5,156,621 A | 10/1992 | Navia et al. |

(Continued)

FOREIGN PATENT DOCUMENTS

EP  0 808 614 A  11/1997

(Continued)

OTHER PUBLICATIONS

PCT Search Report dated Aug. 10, 2003 for PCT Appl. No. PCT/US03/14148.

(Continued)

*Primary Examiner*—Bruce Snow
*Assistant Examiner*—Cheryl Miller
(74) *Attorney, Agent, or Firm*—Vincent J. Serrao

(57) ABSTRACT

The present invention relates to a medical device, and in particular, to a stent-based valve. The valve includes a radially expandable structural frame comprising a proximal anchor and a distal anchor. The proximal and distal anchors are formed from a lattice of interconnected elements, and have a substantially cylindrical configuration with first and second open ends and a longitudinal axis extending there between. The stent based valve also comprises one or more connecting members, each having a first and a second end. The first end of each connecting member is attached to the proximal anchor and the second end of each connecting member is attached to the distal anchor. A biocompatible valve assembly is attached to the proximal anchor and extends distally along the one or more connecting members.

50 Claims, 19 Drawing Sheets

U.S. PATENT DOCUMENTS

| | | | |
|---|---|---|---|
| 5,163,953 A | 11/1992 | Vince | |
| 5,163,955 A | 11/1992 | Love et al. | |
| 5,258,023 A | 11/1993 | Reger | |
| 5,326,370 A | 7/1994 | Love et al. | |
| 5,326,371 A | 7/1994 | Love et al. | |
| 5,344,442 A | 9/1994 | Deac | |
| 5,358,518 A | 10/1994 | Camilli | |
| 5,411,552 A | 5/1995 | Andersen et al. | |
| 5,415,667 A | 5/1995 | Frater | |
| 5,423,887 A | 6/1995 | Love et al. | |
| 5,449,384 A | 9/1995 | Johnson | |
| 5,449,385 A | 9/1995 | Religa et al. | |
| 5,469,868 A | 11/1995 | Reger | |
| 5,480,424 A | 1/1996 | Cox | |
| 5,489,298 A | 2/1996 | Love et al. | |
| 5,500,014 A | 3/1996 | Quijano et al. | |
| 5,549,665 A | 8/1996 | Vessely et al. | |
| 5,554,185 A | 9/1996 | Block et al. | |
| 5,562,729 A | 10/1996 | Purdy et al. | |
| 5,607,463 A | 3/1997 | Schwartz et al. | |
| 5,607,465 A | 3/1997 | Camilli | |
| 5,609,626 A | 3/1997 | Quijano et al. | |
| 5,612,885 A | 3/1997 | Love | |
| 5,662,713 A | 9/1997 | Anderston et al. | |
| 5,695,499 A | 12/1997 | Helgerson et al. | |
| 5,697,382 A | 12/1997 | Love et al. | |
| 5,728,152 A | 3/1998 | Mirsch, II et al. | |
| 5,824,061 A | 10/1998 | Quijano et al. | |
| 5,840,081 A | 11/1998 | Andersen et al. | |
| 5,843,181 A | 12/1998 | Jaffe et al. | |
| 5,851,232 A | 12/1998 | Lois | |
| 5,855,597 A | 1/1999 | Jayaraman | |
| 5,855,601 A | 1/1999 | Bessler et al. | |
| 5,855,602 A | 1/1999 | Angell | |
| 5,861,028 A | 1/1999 | Angelini | |
| 5,876,445 A | 3/1999 | Andersen et al. | |
| 5,895,420 A | 4/1999 | Mirsch, II et al. | |
| 5,910,170 A | 6/1999 | Reimick et al. | |
| 5,928,281 A | 7/1999 | Huynh et al. | |
| 5,935,163 A | 8/1999 | Gabbay | |
| 5,938,696 A | 8/1999 | Goicoechea | |
| 5,957,949 A | 9/1999 | Leonhardt et al. | |
| 5,997,573 A | 12/1999 | Quijano et al. | |
| 6,068,638 A | 5/2000 | Makower | |
| 6,071,277 A | 6/2000 | Farley et al. | |
| 6,086,610 A | 7/2000 | Duerig et al. | |
| 6,124,523 A | 9/2000 | Banas | |
| 6,165,216 A | 12/2000 | Agathos | |
| 6,168,614 B1 | 1/2001 | Andersen et al. | |
| 6,200,336 B1 | 3/2001 | Pavcnix et al. | |
| 6,228,112 B1 | 5/2001 | Klootz et al. | |
| 6,245,100 B1 | 6/2001 | Davila et al. | |
| 6,245,102 B1 | 6/2001 | Jayaramman | |
| 6,283,995 B1 | 9/2001 | Moe et al. | |
| 6,287,334 B1 | 9/2001 | Moll et al. | |
| 6,296,662 B1 | 10/2001 | Caffey | |
| 6,299,637 B1 | 10/2001 | Shaolian et al. | |
| 6,309,413 B1 | 10/2001 | Dereume et al. | |
| 6,315,791 B1 | 11/2001 | Karwoski et al. | |
| 6,355,056 B1 | 3/2002 | Pinheiro | |
| 6,375,787 B1 | 4/2002 | Lukic | |
| 6,440,164 B1 * | 8/2002 | DiMatteo et al. | 623/1.24 |
| 6,458,153 B1 * | 10/2002 | Bailey et al. | 623/1.24 |
| 6,494,909 B2 | 12/2002 | Greenhalgh | |
| 6,893,460 B2 * | 5/2005 | Spenser et al. | 623/2.14 |
| 2001/0010017 A1 * | 7/2001 | Letac et al. | 623/2.11 |
| 2002/0032481 A1 | 3/2002 | Gabbay | |
| 2002/0133183 A1 | 9/2002 | Lentz | |
| 2002/0138135 A1 | 9/2002 | Melzer et al. | |

FOREIGN PATENT DOCUMENTS

| | | |
|---|---|---|
| EP | 0850607 A | 1/1998 |
| EP | 0 928 606 A | 7/1999 |
| EP | 0 938 879 A | 9/1999 |
| EP | 1192957 A2 | 3/2002 |
| FR | 2 788 217 A | 7/2000 |
| WO | WO 00 47136 A | 8/2000 |
| WO | WO 00 47139 A | 8/2000 |
| WO | WO 01/28459 A | 4/2001 |
| WO | WO 01 49213 A | 7/2001 |
| WO | WO 01 49213 A2 | 7/2001 |
| WO | WO 01 67992 A | 9/2001 |
| WO | WO 02/26139 A1 | 4/2002 |

OTHER PUBLICATIONS

PCT Search Report dated Feb. 9, 2003 for PCT Appl. No. PCT/US03/14009.

PCT Search Report dated Dec. 9, 2003 for PCT Appl. No. PCT/US03/14530.

PCT Search report dated Feb. 9, 2003 for PCT Appl. No. PCT/US03/14115.

Search Report for PCT Application No. US03/15323 dated Jun. 4, 2004.

International Search Report dated Sep. 2, 2003 for related application PCT/US03/14008.

D. Stoeckel, et al. "A Survey of Stent Designs", Correspondence: D. Stoeckel, Nitinol Devices & Components, a Johnson & Johnson company 27533 Westinghouse Drive, Fremont, CA 94539, USA.

* cited by examiner

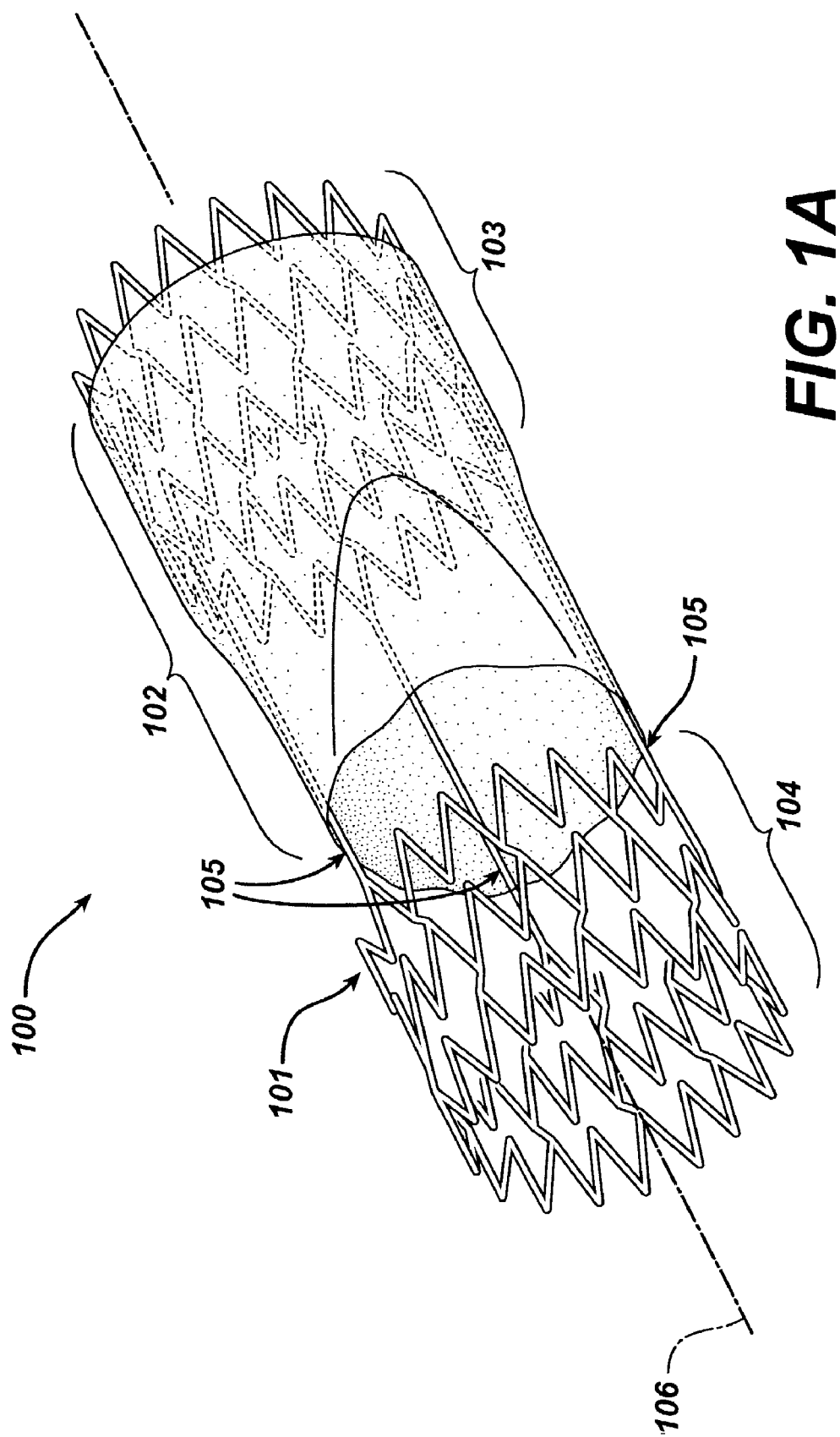

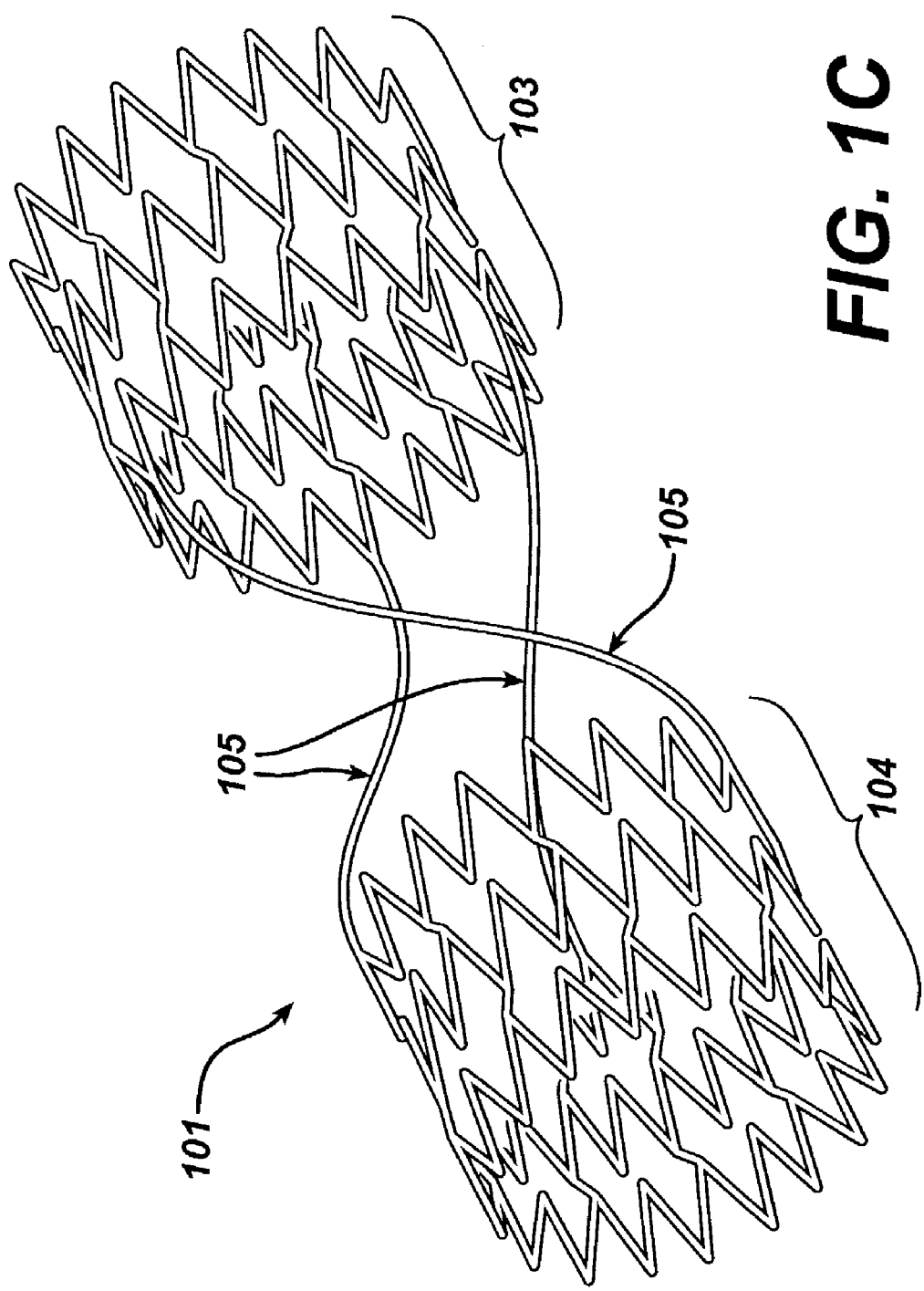

FRAME BASED UNIDIRECTIONAL FLOW PROSTHETIC IMPLANT

CROSS-REFERENCE TO RELATED APPLICATION

This application claims the benefit of U.S. Provisional Application Ser. No. 60/379,604, filed May 10, 2002.

FIELD OF THE INVENTION

The present invention relates to a medical device, and more particularly to a frame based unidirectional flow prosthetic valve, and the method for fabricating such valve.

BACKGROUND OF RELATED ART

The human body has numerous biological valves that control fluid flow through body lumens and vessels. For example the circulatory system has various heart valves that allow the heart to act as a pump by controlling the flow of blood through the heart chambers, veins, and aorta. In addition, the venous system has numerous venous valves that help control the flow of blood back to the heart, particularly from the lower extremities.

These valves can become incompetent or damaged by disease, for example, phlebitis, injury, or the result of an inherited malformation. Heart valves are subject to disorders, such as mitral stenosis, mitral regurgitation, aortic stenosis, aortic regurgitation, mitral valve prolapse and tricuspid stenosis. These disorder are potentially life threatening. Similarly, incompetent or damaged venous valves usually leak, allowing the blood to improperly flow back down through veins away from the heart (regurgitation reflux or retrograde blood flow). Blood can then stagnate in sections of certain veins, and in particular, the veins in the lower extremities. This stagnation of blood raises blood pressure and dilates the veins and venous valves. The dilation of one vein may in turn disrupt the proper function of other venous valves in a cascading manner, leading to chronic venous insufficiency.

Numerous therapies have been advanced to treat symptoms and to correct incompetent valves. Less invasive procedures include compression, elevation and wound care. However, these treatments tend to be somewhat expensive and are not curative. Other procedures involve surgical intervention to repair, reconstruct or replace the incompetent or damaged valves, particularly heart valves.

Surgical procedures for incompetent or damaged venous valves include valvuloplasty, transplantation, and transposition of veins. However, these surgical procedures provide somewhat limited results. The leaflets of some venous valves are generally thin, and once the valve becomes incompetent or destroyed, any repair provides only marginal relief.

As an alternative to surgical intervention, drug therapy to correct valvular incompetence has been utilized. Currently, however, there are no effective drug therapies available.

Other means and methods for treating and/or correcting damaged or incompetent valves include utilizing xenograft valve transplantation (monocusp bovine pericardium), prosthetic/bioprosthetic heart valves and vascular grafts, and artificial venous valves. These means have all had somewhat limited results.

What is needed is an artificial endovascular valve for the replacement of incompetent biological human valves, particularly heart and venous valves. These valves may also find use in artificial hearts and artificial heart assist pumps used in conjunction with heart transplants.

SUMMARY OF THE INVENTION

The present invention relates to a medical device, and in particular, to a stent-based valve. One embodiment of the invention comprises a radially expandable structural frame including a proximal anchor and a distal anchor. The proximal and distal anchors are formed from a lattice of interconnected elements, and have a substantially cylindrical configuration with first and second open ends and a longitudinal axis extending there between.

The stent based valve also comprises one or more connecting members, each having a first and a second end. The first end of each connecting member is attached to the proximal anchor and the second end of each connecting member is attached to the distal anchor. A biocompatible valve assembly having a substantially cylindrical shape is attached to the proximal anchor and extends distally along the one or more connecting members.

In another embodiment of the invention, the stent based valve comprises a radially expandable structural frame including a proximal anchor and a distal anchor. The proximal and distal anchors are formed from a lattice of interconnected elements, and have a substantially cylindrical configuration with first and second open ends and a longitudinal axis extending there between.

The stent based valve also comprises one or more connecting members, each having a first and a second end. The first end of each connecting member is attached to the proximal anchor and the second end of each connecting member is attached to the distal anchor. A biocompatible valve assembly is attached to the proximal anchor and extends distally along the one or more connecting members. A limiting means is integrated into the distal end of the biocompatible membrane assembly to limit sliding movement between the membrane assembly and connecting member.

In still another embodiment of the invention, the stent-based valve comprises a radially expandable structural frame including a proximal anchor and a distal anchor. The proximal and distal anchors are formed from a lattice of interconnected elements, and have a substantially cylindrical configuration with first and second open ends and a longitudinal axis extending there between.

The stent based valve also comprises one or more connecting members, each having a first and a second end. The first end of each connecting member is attached to the proximal anchor and the second end of each connecting member is attached to the distal anchor. A biocompatible valve assembly is attached to the proximal anchor and extends distally along the one or more connecting members.

BRIEF DESCRIPTION OF THE DRAWINGS

FIG. 1A shows a perspective view of a prosthetic venous valve in the deployed state according to one embodiment of the present invention.

FIG. 1C shows a perspective view of the prosthetic venous valve structural frame having helical connecting members according to one embodiment of the present invention.

DETAILED DESCRIPTION OF THE PREFERRED EMBODIMENTS

The stent-based valves of the present invention provide a method for overcoming the difficulties associated with the treatment of valve insufficiency. Although stent based venous valves are disclosed to illustrate one embodiment of the present invention, one of ordinary skill in the art would understand that the disclosed invention can be equally applied to other locations and lumens in the body, such as, for example, coronary, vascular, non-vascular and peripheral vessels, ducts, and the like, including but not limited to cardiac valves, venous valves, valves in the esophagus and at the stomach, valves in the ureter and/or the vesica, valves in the biliary passages, valves in the lymphatic system and valves in the intestines.

In accordance with one aspect of the present invention, the prosthetic valve is designed to be percutaneously delivered through a body lumen to a target site by a delivery catheter. The target site may be, for example, a location in the venous system adjacent to an insufficient venous valve. Once deployed the prosthetic venous valve functions to assist or replace the incompetent or damaged natural valve by allowing normal blood flow (antegrade blood flow) and preventing or reducing backflow (retrograde blood flow).

A perspective view of a prosthetic venous valve in the expanded (deployed) state according to one embodiment of the present invention is shown in FIG. 1A. The prosthetic venous valve 100 comprises a structural frame 101 and a biocompatible membrane assembly 102. In one embodiment, the membrane assembly 102 is comprised of a tubular membrane, valve flaps and valve cusps. The flaps and cusps may be independent components attached to the tubular membrane to form the membrane assembly 102, but are preferably part of, and integrated into, the tubular membrane. In a preferred embodiment, the valve flaps and valve cusps are formed into the tubular membrane by processing techniques as will be discussed in greater detail below.

Figure 1B:
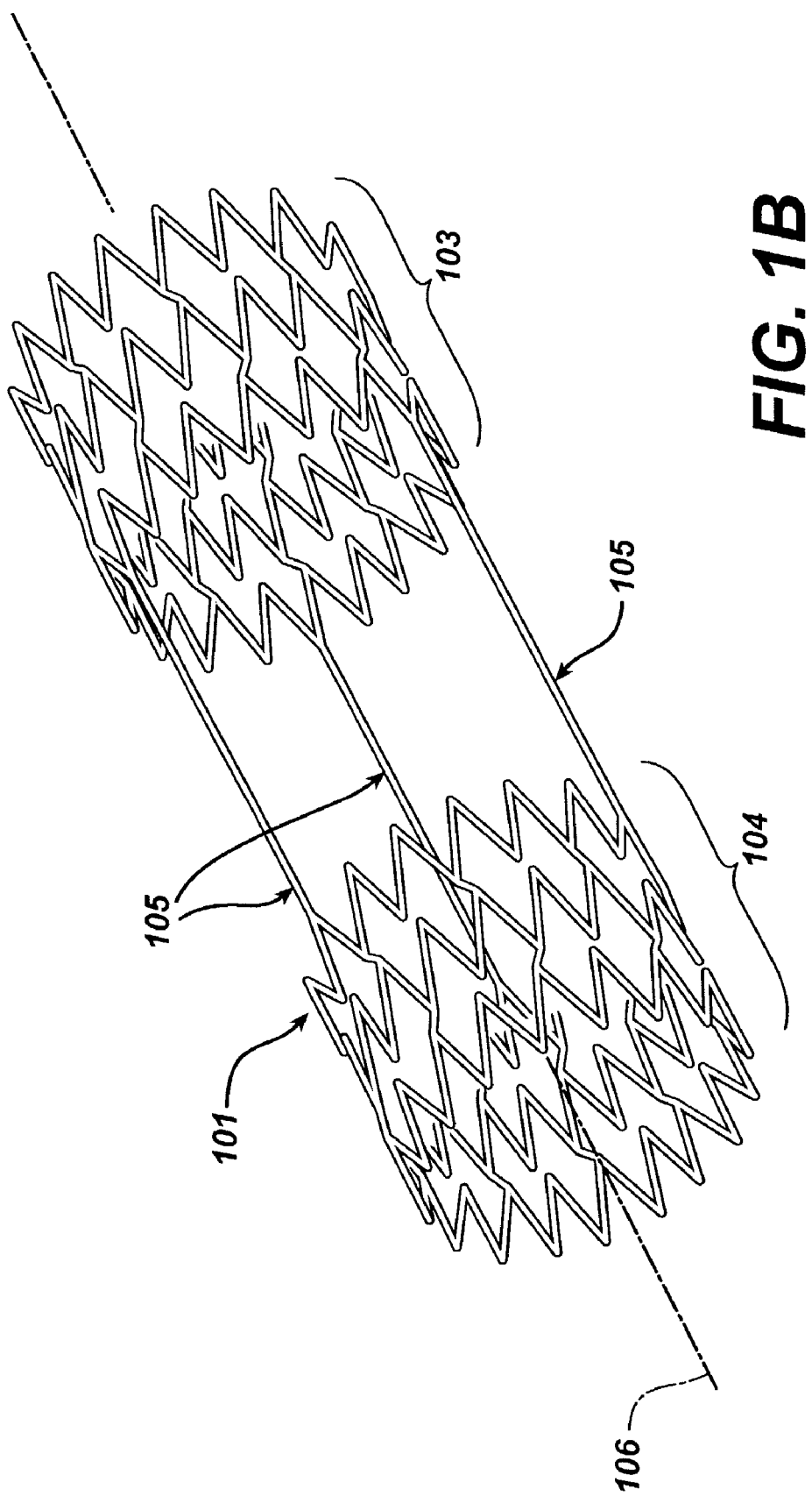
FIG. 1B shows a perspective view of the prosthetic venous valve structural frame in the deployed state according to one embodiment of the present invention.

For clarity, a perspective view of the prosthetic venous valve 100 structural frame 101 is shown in FIG. 1B. The structural frame 101 consists of proximal and distal anchor structures 103, 104 connected by at least one connecting member 105. In a preferred embodiment, at least three connecting members 105 are utilized.

It should be noted that the terms proximal and distal are typically used to connote a direction or position relative to a human body. For example, the proximal end of a bone may be used to reference the end of the bone that is closer to the center of the body. Conversely, the term distal can be used to refer to the end of the bone farthest from the body. In the vasculature, proximal and distal are sometimes used to refer to the flow of blood to the heart, or away from the heart, respectively. Since the prosthetic valves described in this invention can be used in many different body lumens, including both the arterial and venous system, the use of the terms proximal and distal in this application are used to describe relative position in relation to the direction of fluid flow. For example, the use of the term proximal anchor in the present application describes the upstream anchor of structural frame 101 regardless of its orientation relative to the body. Conversely, the use of the term distal is used to describe the down stream anchor on structural frame 101 regardless of its orientation relative to the body. Similarly, the use of the terms proximal and distal to connote a direction describe upstream (retrograde) or downstream (antegrade) respectively.

The connecting members 105 are attached between the proximal and distal anchors 103, 104 to further support the biocompatible membrane assembly 102 (not shown in FIG. 1B). In one embodiment, the connecting members 105 are substantially straight members, connecting the stent based proximal and distal anchors 103, 104 in a direction substantially parallel to the longitudinal axis 106. Although three connecting members 105 are shown in the illustrated embodiment, this configuration should not be construed to limit the scope of the invention.

Alternatively, the connecting members 105 may be twisted in a helical fashion as they extend from the proximal to distal anchors 103, 104. This alternate embodiment is illustrated in FIG. 1C. Specifically, the connection points between the connecting members 105 and the distal anchor 104, and the connecting members 105 and the proximal anchor 103, are rotationally phased 180 degrees from each other to provide the helical design.

Figure 1D:
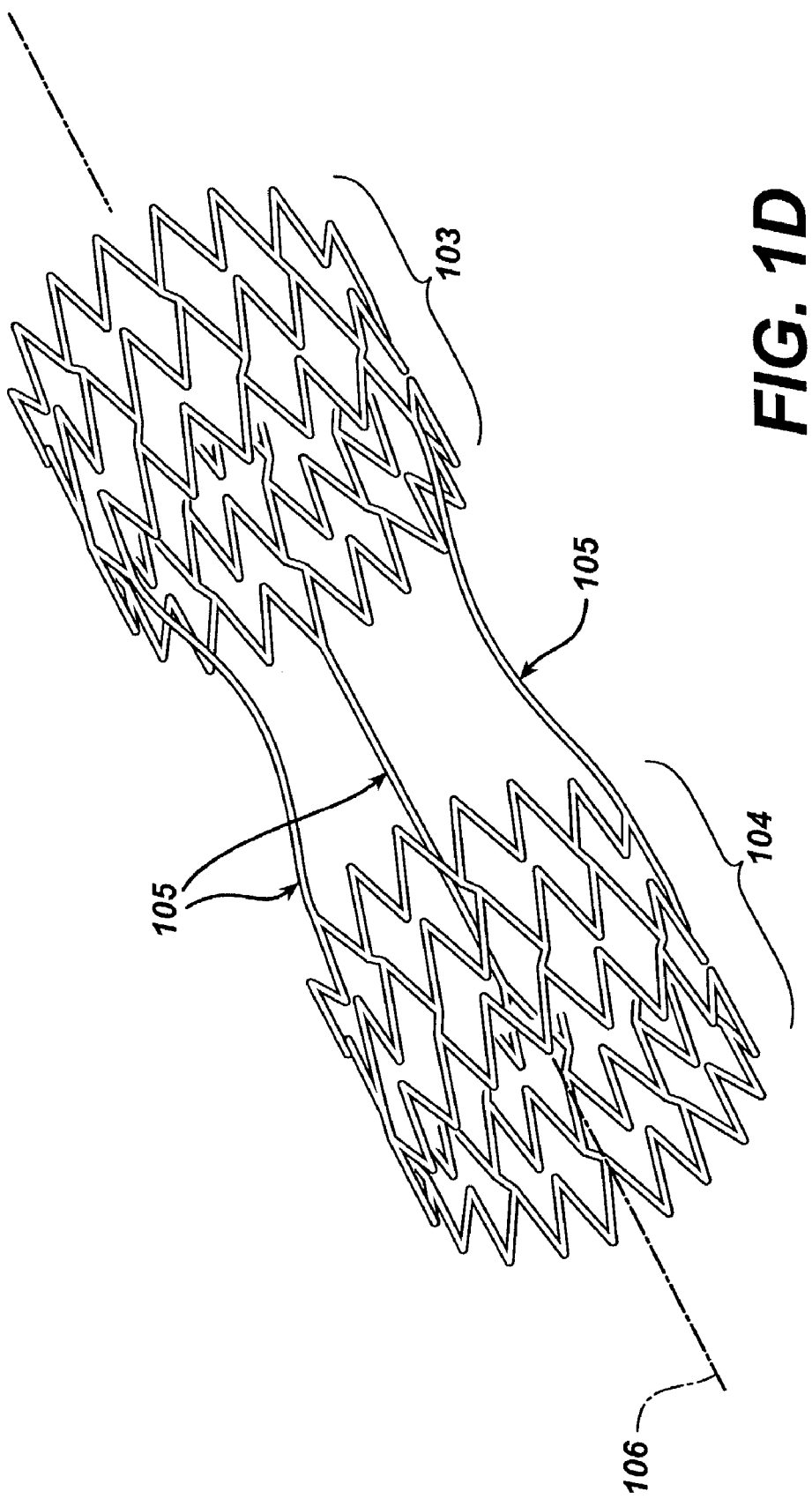
FIG. 1D shows a perspective view of the prosthetic venous valve structural frame having an hourglass shape according to one embodiment of the present invention.

Each connecting member 105 may also be biased inward slightly toward the longitudinal centerline 106 of the stent-based anchors 103, 104, creating a structural frame 101 having an hour-glass shape with the minimum radius located substantially at the longitudinal midpoint along the connecting member 105 length. An hourglass shaped structural frame 101 is illustrated in FIG. 1D.

The materials for the structural frame 101 should exhibit excellent corrosion resistance and biocompatibility. In addition, the material comprising the structural frame 101 should be sufficiently radiopaque and create minimal artifacts during MRI.

The present invention contemplates deployment of the prosthetic venous valve 100 by both assisted (mechanical) expansion, i.e. balloon expansion, and self-expansion means. In embodiments where the prosthetic venous valve 100 is deployed by mechanical (balloon) expansion, the structural frames 101 is made from materials that can be plastically deformed through the expansion of a mechanical assist device, such as by the inflation of a catheter based balloon. When the balloon is deflated, the frame 101 remains substantially in the expanded shape. Accordingly, the ideal material has a low yield stress (to make the frame 101 deformable at manageable balloon pressures), high elastic modulus (for minimal recoil), and is work hardened through expansion for high strength. The most widely used material for balloon expandable structures 101 is stainless steel, particularly 316L stainless steel. This material is particularly corrosion resistant with a low carbon content and additions of molybdenum and niobium. Fully annealed, stainless steel is easily deformable.

Alternative materials for mechanically expandable structural frames 101 that maintain similar characteristics to stainless steel include tantalum, platinum alloys, niobium alloys, and cobalt alloys. In addition other materials, such as polymers and bioabsorbable polymers may be used for the structural frames 101.

Where the prosthetic venous valve 100 is self-expanding, the materials comprising the structural frame 101 should exhibit large elastic strains. A suitable material possessing this characteristic is Nitinol, a Nickel-Titanium alloy that can recover elastic deformations of up to 10 percent. This unusually large elastic range is commonly known as superelasticity.

The disclosure of various materials comprising the structural frame should not be construed as limiting the scope of the invention. One of ordinary skill in the art would understand that other material possessing similar characteristics may also be used in the construction of the prosthetic venous valve 100. For example, bioabsorbable polymers, such as polydioxanone may also be used. Bioabsorbable materials absorb into the body after a period of time, leaving only the biocompatible membrane 102 in place. The period of time for the structural frame 101 to absorb may vary, but is typically sufficient to allow adequate tissue growth at the implant location to adhere to and anchor the biocompatible membrane 102.

The structural frame 101 may be fabricated using several different methods. Typically, the structural frame 101 is constructed from sheet, wire (round or flat) or tubing, but the method of fabrication generally depends on the raw material form used.

The structural frame 101 can be formed from wire using convention wire forming techniques, such as coiling, braiding, or knitting. By welding the wire at specific locations a closed-cell structure may be created. This allows for continuous production, i.e. the components of the structural frame 101, such as proximal and distal anchors 103, 104, may be cut to length from a long wire mesh tube. The connecting member 105 may then be attached to the proximal and distal anchors 103, 104 by welding or other suitable connecting means.

In addition, the complete frame structure may be cut from a solid tube or sheet of material, and thus the structural frame 101 would be considered a monolithic unit. Laser cutting, water-jet cutting and photochemical etching are all methods that can be employed to form the structural frame 101 from sheet and tube stock.

As discussed above, the disclosure of various methods for constructing the structural frame 101 should not be construed as limiting the scope of the invention. One of ordinary skill in the art would understand that other construction methods may be employed to form the structural frame 101 of the prosthetic venous valve 100.

In one embodiment of the invention, the anchors 103, 104 are stent-based structures. This configuration facilitates the percutaneous delivery of the prosthetic venous valve 100 through the vascular system in a compressed state. Once properly located, the stent-based venous valve 100 may be deployed to the expanded state.

Figure 2A:
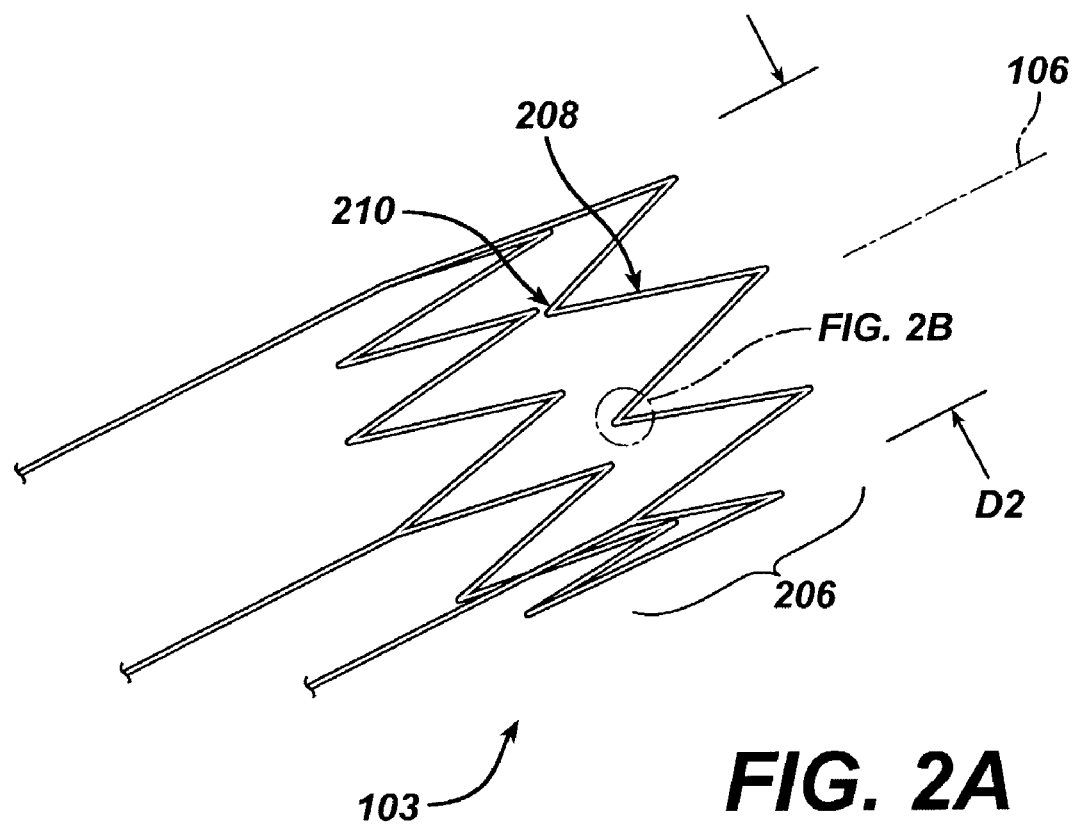
FIG. 2A shows a perspective view of the proximal stent-based anchor in the expanded deployed state according to one embodiment of the present invention.

A perspective views of a typical stent-based anchor in the expanded (deployed) state is shown in FIG. 2A. Although a Z or S shaped pattern stent anchor is shown for the purpose of example, the illustration is not to be construed as limiting the scope of the invention. One of ordinary skill in the art would understand that other stent geometries may be used.

The stent anchors (proximal and distal anchors 103, 104 respectively) each comprise a tubular configuration of structural elements having proximal and distal open ends and defining a longitudinal axis 106 extending therebetween. The stent anchors 103, 104 have a first diameter (not shown) for insertion into a patient and navigation through the vessels, and a second diameter D2 for deployment into the target area of a vessel, with the second diameter being greater than the first diameter. The stent anchors 103, 104, and thus the stent based venous valve 100, may be either a mechanical (balloon) or self-expanding stent based structure.

Figure 2B:
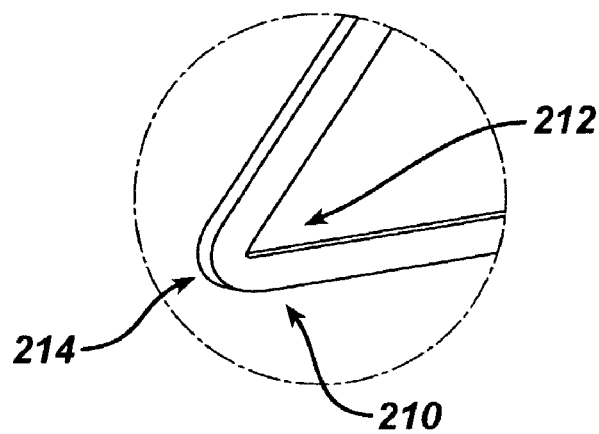
FIG. 2B shows a close-up perspective view of a loop having inner and outer radii according to one embodiment of the present invention.

Each stent anchor 103, 104 comprises at least one hoop structure 206 extending between the proximal and distal ends. The hoop structure 206 includes a plurality of longitudinally arranged strut members 208 and a plurality of loop members 210 connecting adjacent struts 208. Adjacent struts 208 are connected at opposite ends in a substantially S or Z shaped pattern so as to form a plurality of cells. As previously discussed, one of ordinary skill in the art would recognize that the pattern shaped by the struts is not a limiting factor, and other shaped patterns may be used. The plurality of loops 210 have a substantially semi-circular configuration, having an inter radii 212 and outer radii 214, and are substantially symmetric about their centers. The inner and outer radii 212, 214 respectively, are shown in a close-up perspective view illustrated in FIG. 2B.

Figure 2C:
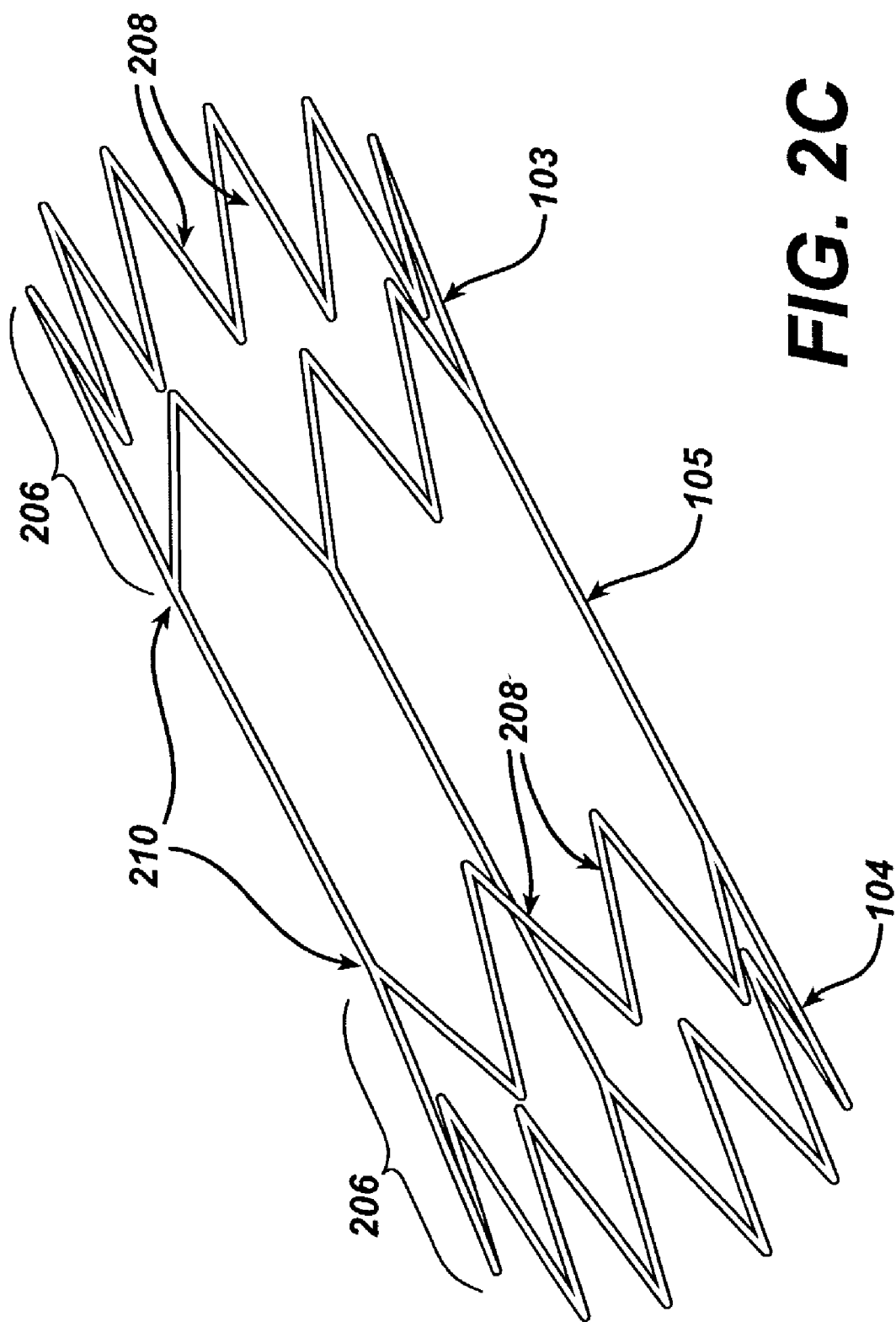
FIG. 2C shows a perspective view of the prosthetic venous valve structural frame having connecting members connected between the proximal and distal anchors in a peak-to-peak configuration according to one embodiment of the present invention.

The connecting member 105 may be connected to the proximal and distal anchors 103, 104 at various points along the structure. As illustrated in FIG. 2C, the connecting members 105 are connected between the proximal end of the distal anchor 104 and the distal end of the proximal anchor 103 at the inflection point of the loop members 210. This configuration creates a "Peak-to-Peak" connection bridging the outer radii 214 of the inflection point of loop members 210 on the proximal anchor 103 with the outer radii 214 of the inflection point of the loop member 210 on the distal anchor 104.

Preferably the connecting members 105 are connected to the inflection point of loop members 210 oriented directly opposite one another, and are evenly spaced along the circumference of the tubular anchors 103, 104. This configuration facilitates the radial expansion of the prosthetic valve from the collapsed (delivered) state to the expanded (deployed) state, and provides a substantially symmetrical valve configuration.

Figure 2D:
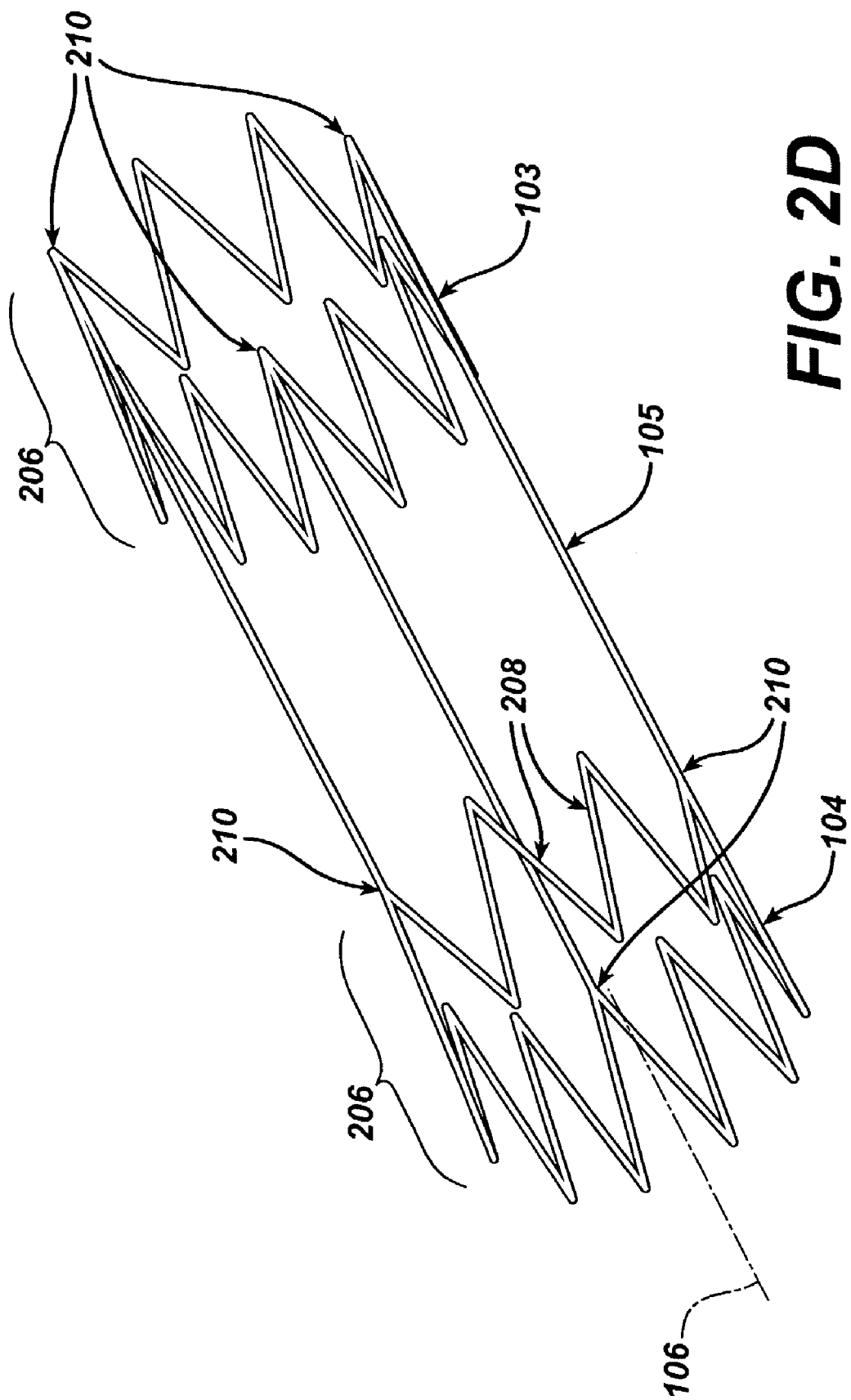
FIG. 2D shows a perspective view of the prosthetic venous valve structural frame having connecting members connected between the distal and proximal anchors in a peak-to-valley configuration according to one embodiment of the present invention.

Alternatively, the connecting members 105 may be connected between the distal and proximal anchors 104, 103 to create a "Peak-to-Valley" connection between the loop members 210. In this configuration, illustrated in FIG. 2D, the connecting members 105 are connected to the proximal end of the distal anchor 104 at the outer radii 214 of the inflection point of loop member 210, and the inner radii 212 of the inflection point of loop member 210 on the proximal end of the proximal anchor 103.

Figure 2E:
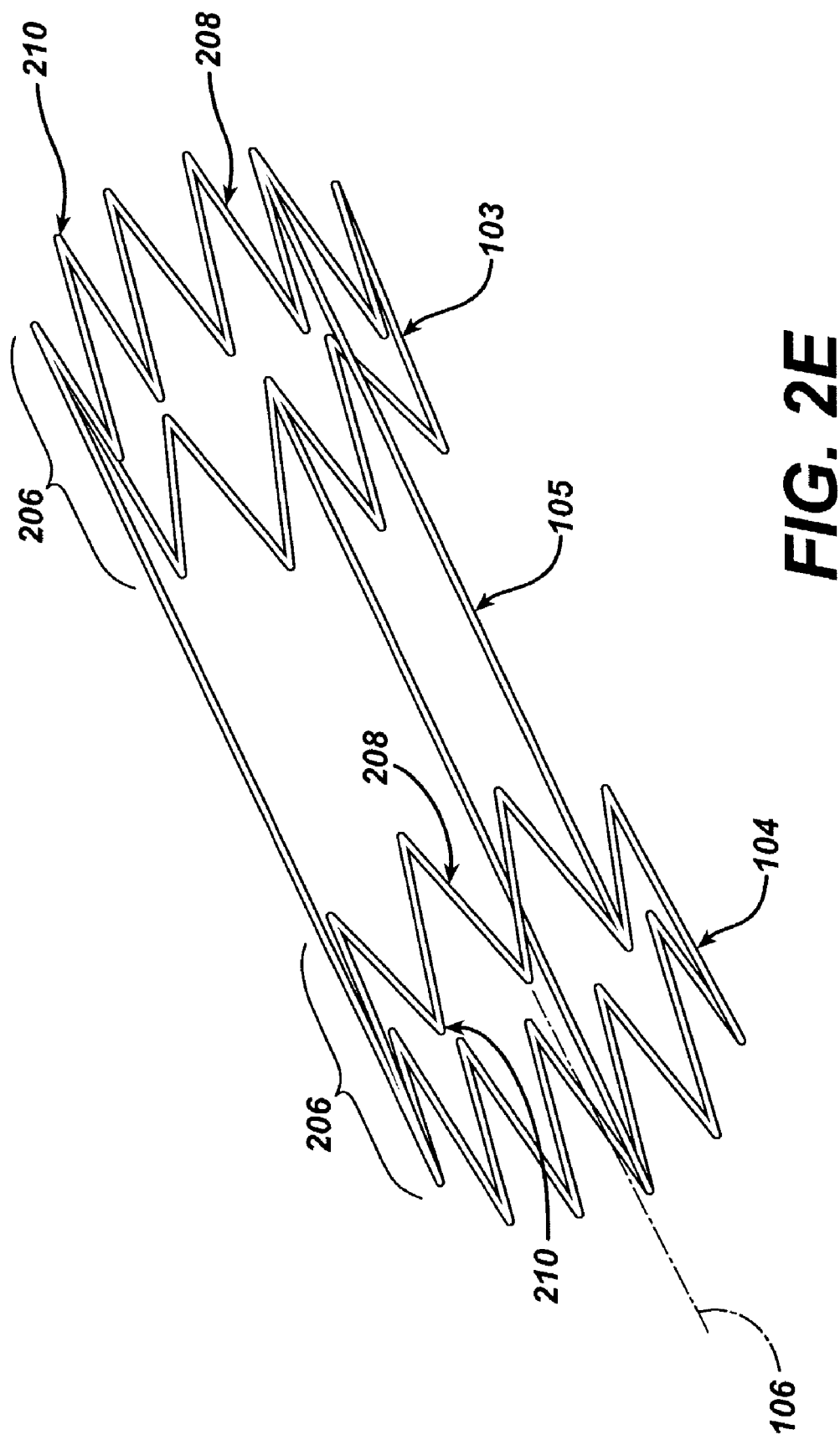
FIG. 2E shows a perspective view of the prosthetic venous valve structural frame having connecting members connected between the distal and proximal anchors in a valley-to-valley configuration according to one embodiment of the present invention.

In a further embodiment, the connecting members 105 may be connected between the distal end of the distal anchor 104 and the proximal end of the proximal anchor 103 at the inflection point of the loop members 210 as shown in FIG. 2E. This configuration creates a "Valley-to-Valley" connection bridging the inner radii 212 of the inflection point of loop members 210 on the proximal anchor 103 with the inner radii 212 of the inflection point of the loop member 210 on the distal anchor 104.

Figure 2F:
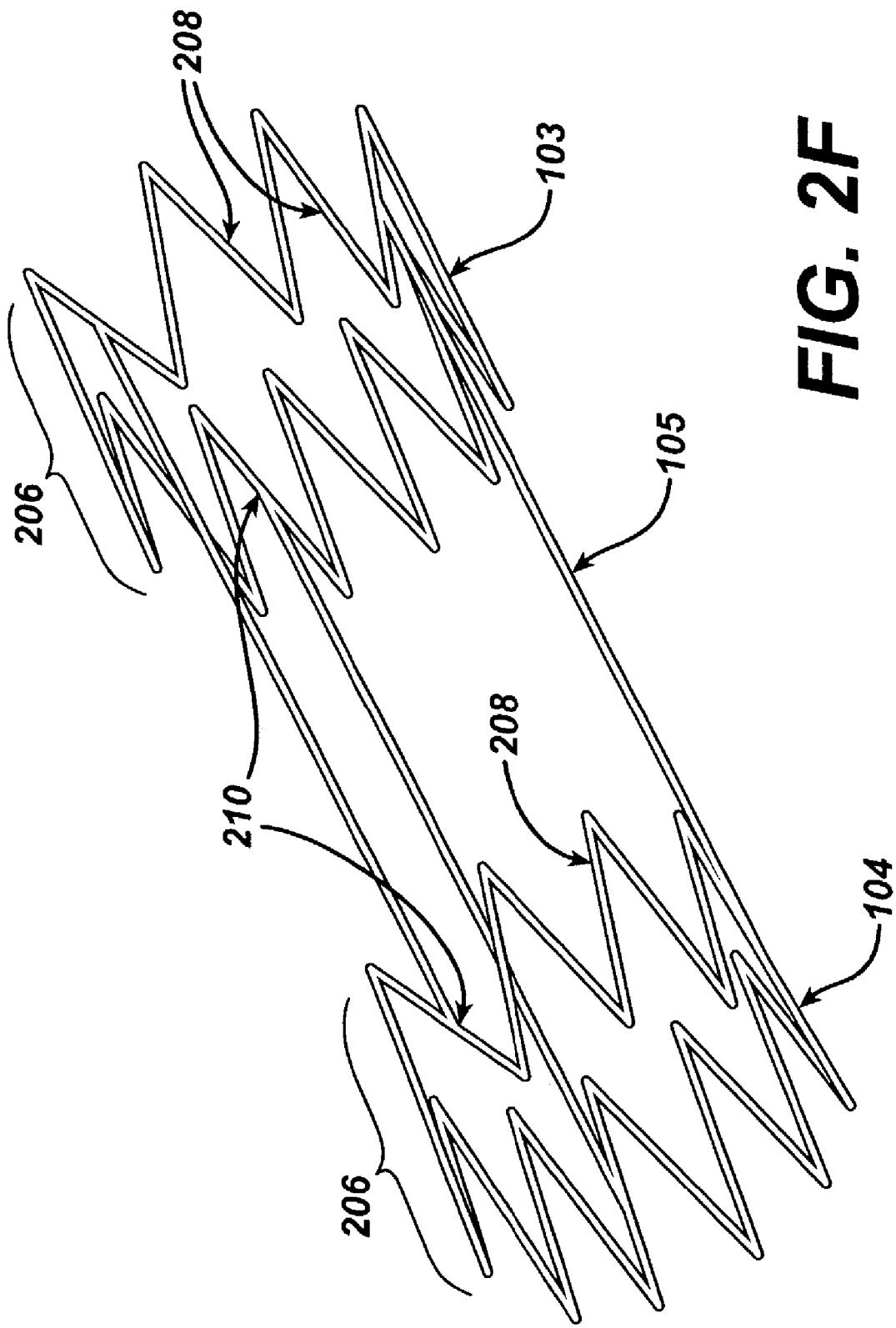
FIG. 2F shows a perspective view of the prosthetic venous valve structural frame having connecting members connected between the distal and proximal anchors along the strut members according to one embodiment of the present invention.

In still a further embodiment, the connecting members 105 may be connected between the strut members 208 of the distal anchor 104 and the strut members 208 of the proximal anchor 103 as shown in FIG. 2F.

In any of the above described configurations, the connections between the connecting members 105 and the anchors 103, 104 may be made at every inflection point around the circumference of the structure; or alternatively, at a subset of the inflection points around the circumference of the structure. In other words, connected inflection points alternate with unconnected inflection points in some defined pattern.

Although stent anchors 103, 104 incorporating a singular hoop structure are shown in the embodiment illustrated in FIGS. 2A though 2F, each stent anchor may utilize a plurality of hoop structures.

Figure 3:
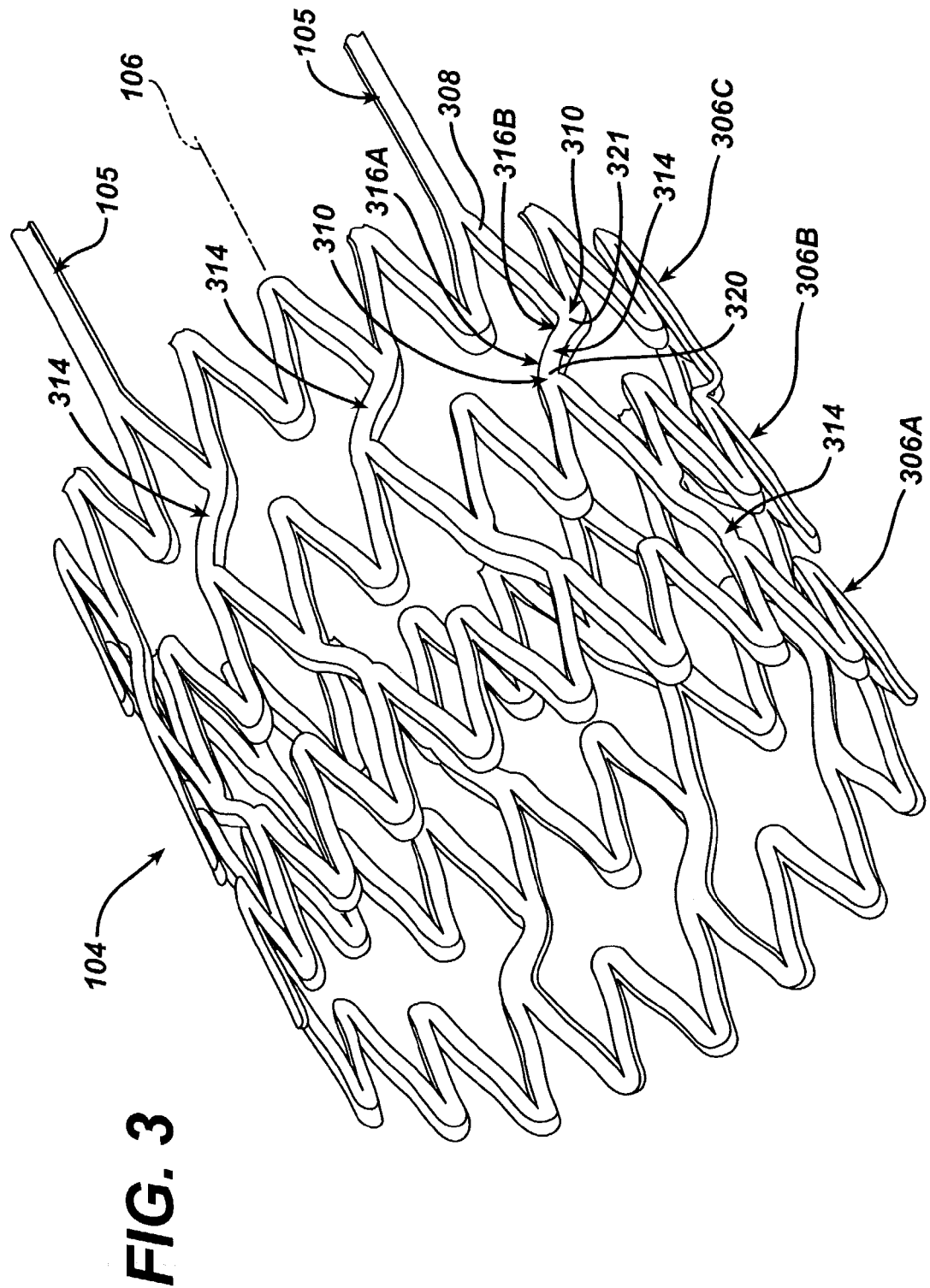
FIG. 3 shows a perspective view of the distal stent anchor having a plurality of hoop structures according to one embodiment of the present invention.

FIG. 3 shows a distal anchor having a plurality of hoop structures 306A through 306C according to another embodiment of the present invention. In the illustrated embodiment, the distal stent anchor 104 may further comprise a plurality of bridge members 314 that connect adjacent hoops 306A through 306C. Each bridge member 314 comprises two ends 316A, 316B. One end 316A, 316B of each bridge 314 is attached to one loop on one hoop. Using hoop sections 306B and 306C for example, each bridge member 314 is connected at end 316A to loop 310 on hoop section 306B at a point 320. Similarly, the opposite end 316B of each bridge member 314 is connected to loop 310 on hoop sections 306C at a point 321.

The proximal and distal anchors 103, 104 secure the prosthetic valve 100 to the inside wall of a body vessel such as a vein, and provide anchor points for the connecting members 105. Once deployed in the desired location, the anchors 103, 104 will expand to an outside diameter slightly larger that the inside diameter of the native vessel (not shown) and remain substantially rigid in place, anchoring the valve assembly to the vessel. The connecting members 105 preferably have an inferior radial stiffness, and will conform much more closely to the native diameter of the vessel, facilitating the operation of the biocompatible membrane assembly 102.

The membrane assembly is formed from a flexible membrane-like biocompatible material that is affixed to the frame structure 101. The membrane must be strong enough to resist tearing under normal use, yet thin enough to provide the necessary flexibility that allows the biocompatible membrane assembly 102 to open and close satisfactorily.

Figures 4A, 4B:
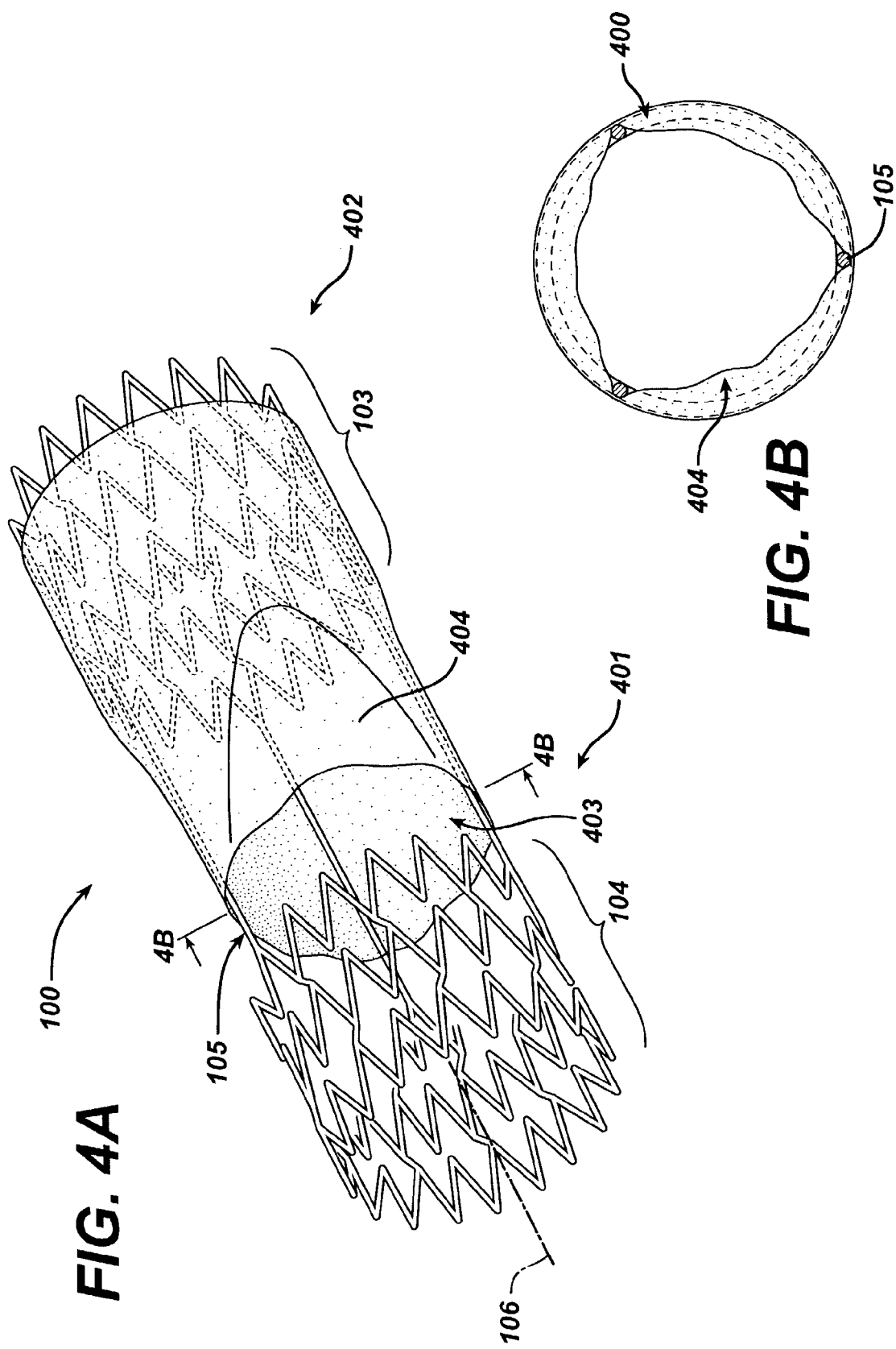
FIG. 4A is a perspective view illustrating one embodiment of the expanded (deployed) prosthetic venous valve assembly in the open position.
FIG. 4B is a section view illustrating one embodiment of the expanded (deployed) prosthetic venous valve assembly in the open position.

FIGS. 4A and 4B are perspective and section views, respectively, illustrating one embodiment of the expanded (deployed) prosthetic venous valve assembly 100 in the open position. The membrane material may be a biological material, such as a vein or small intestine submucosa (SIS), but is preferably a synthetic material such as a polymer, for example an elastic or elastomeric polymer, including a fluoropolymer, fluoroelastomer, or a bioabsorbable material, such as a bioabsorbable polymer or bioabsorbable elastomer. Bioabsorbable materials may allow cells to grow and form a tissue membrane (or valve flaps) over the bioabsorbable membrane. The bioabsorbable membrane then absorbs into the body, leaving the tissue membrane and/or flaps in place to act as a new natural tissue valve.

To achieve the necessary flexibility and strength of the membrane assembly 102, the synthetic material may be reinforced with a fiber, such as an electro-statically spun (ESS) fiber, porous foam, such as ePTFE, or mesh. The flexible membrane like biocompatible material is formed into a tube (membrane tubular structure 400) and placed over and around the structural frame 101. The membrane tubular structure 400 has a first (distal) and second (proximal) ends 401, 402 respectively, and preferably also has integrated valve flaps 403 and valve cusps 404. These components together comprise the membrane assembly 102.

The first end 401 of the membrane tubular structure 400 is located between the proximal and distal anchors 103, 104, and is preferably located at the approximate longitudinal midpoint of the connecting members 105 between the two anchors 103, 104. The second end 402 of the membrane tubular structure 400 extends proximally from the longitudinal midpoint, and is preferably located proximal to at least one half of the proximal anchor 103. In one embodiment of the invention, the membrane structure 400 completely covers the proximal anchor 103. This configuration allows the proximal anchor 103 to expand the membrane tubular structure 400 into the native vessel wall, anchoring the membrane tubular structure 400 in place, and providing adequate sealing against retrograde blood flow.

The distal end 401 of the membrane tubular structure 400 terminates with the valve flaps 403. The number of valve flaps 403 is directly proportional to the number of connecting members 105 supporting the membrane tubular assembly 102. The valve flaps 403 are sufficiently pliable and supple to easily open and close as the blood flow changes from antegrade to retrograde. When the valve flaps 403 close (during retrograde flow) the interior surfaces of the flaps 403 and/or membrane tubular structure 400 come into contact to prevent or adequately reduce retrograde blood flow.

To facilitate closing the valve flaps 403 during retrograde blood flow, valve cusps 404 are formed into the membrane tubular structure 400. The valve cusps 404 are defined generally by the intersection of the connecting members 105 and membrane tubular structure 400.

The use of the term "cusps" is not meant to limit the scope of this invention. Although the term "cusps" is often more aptly used to describe the valve members in semilunar valves, such as the aortic and pulmonary valves, this discussion refers to both the cusps of semilunar valves and the "leaflets" of venous and atrioventricular valves. Accordingly, it should be understood that the aspects discussed in relation to these valves could be applied to any type of mammalian valve, including heart valves, venous valves, peripheral valves, etc.

Figures 5A, 5B:
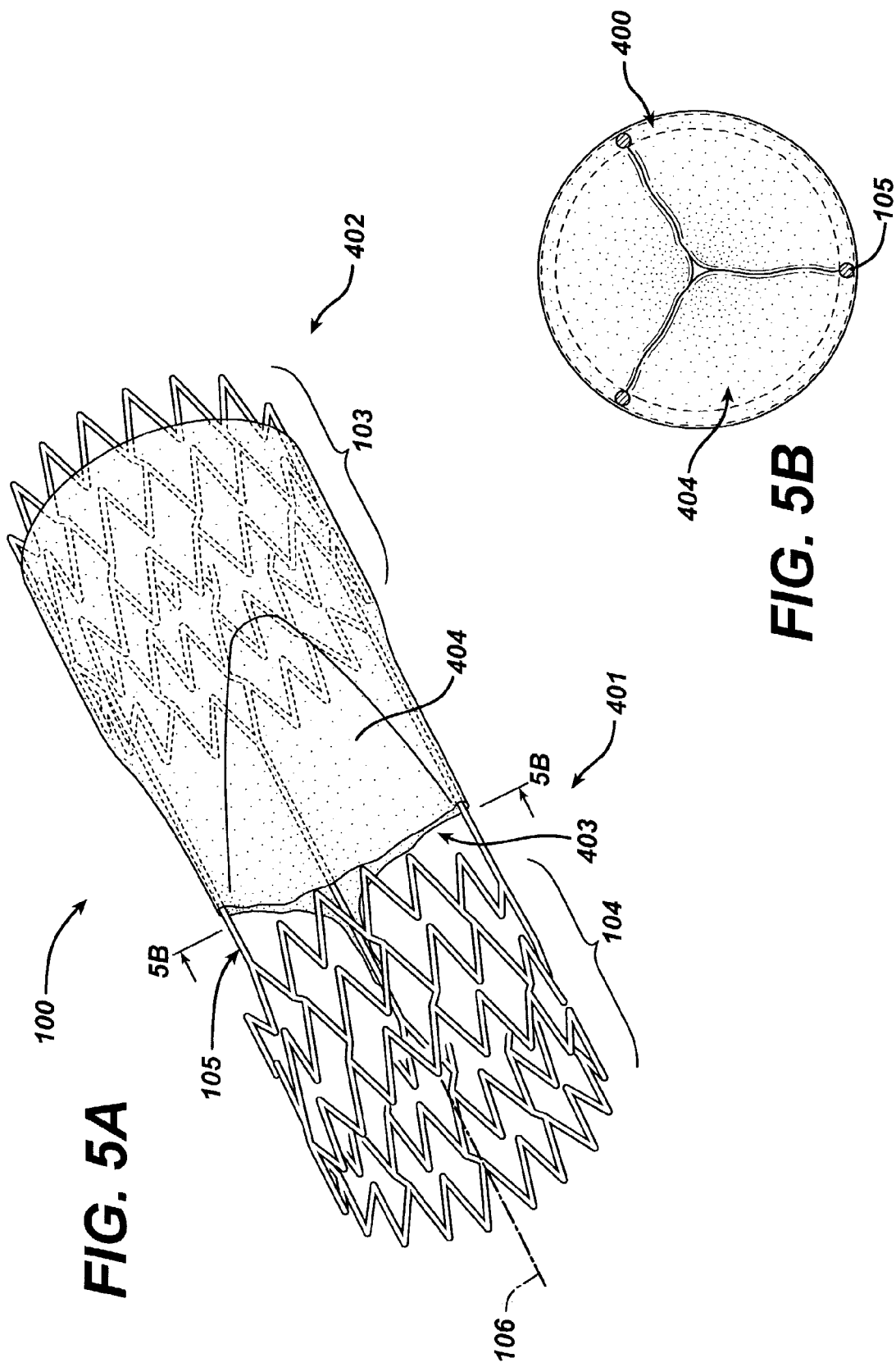
FIG. 5A is a perspective view illustrating one embodiment of the expanded (deployed) prosthetic venous valve assembly in the closed position.
FIG. 5B is a section view illustrating one embodiment of the expanded (deployed) prosthetic venous valve assembly in the closed position.

During retrograde flow, blood passes the leading edge of valve flaps 403 and enters the valve cusps 404. Since the membrane tubular structure 400 (and membrane assembly 102) are substantially sealed against the inner vessel wall by proximal anchor 103, the valve cusps 404 form a substantially fluid tight chamber. As the valve cusps 404 fill, the membrane tubular structure 400 is directed inward until the interior surfaces of the membrane tubular structure 400 contact each other, particularly along the leading edges of valve flaps 403, closing the membrane assembly 102. FIGS. 5A and 5B show perspective and section views, respectively, illustrating one embodiment of the expanded (deployed) prosthetic venous valve assembly 100 in the closed position.

In a preferred embodiment of the invention, the membrane assembly 102 is normally configured in the open position, and only moves to the closed position upon retrograde blood flow. This configuration minimizes interference with blood flow (minimized blocking) and reduces turbulence at and through the valve. The connecting members 105 in this embodiment have an inferior radial stiffness, and provide a natural bias against the movement of the membrane assembly 102 to the closed position. This bias assists the valve flaps 403 and valve cusps 404 when returning to the open position.

Depending on the application, it may also be desired that the bias towards opening the membrane assembly 102 (against closing) be sufficiently high to commence opening the valve before antegrade blood flow begins, i.e. during a point in time when the blood flow is stagnant (there is neither antegrade nor retrograde blood flow), or when minimal retrograde flow is experienced.

In other applications, it may be desirable to have the valve assembly normally configured in the closed position, biased closed, and only open upon antegrade flow.

As earlier described, the membrane assembly 102 is made from a flexible membrane-like biocompatible material formed into the membrane tubular structure 400. The membrane 400 can be woven, non-woven (such as electrostatic spinning), mesh, knitted, film or porous film (such as foam).

The membrane assembly 102 may be fixedly attached to the structural frame by many different methods, including attachment resulting from radial pressure of the structural frame 101 against the membrane assembly 102, attachment by means of a binder, heat, or chemical bond, and/or attachment by mechanical means, such as welding or suturing. Preferably some of the membrane assembly 102, such as distal end 401 of tubular membrane 400, is slideably attached to the structural frame 101, particularly along connecting members 105. Allowing the distal end 401 to slide along the connecting members 105 may allow or improve the opening and closing of the flaps 403. The sliding movement may also assist the cusps 404 when filling and emptying.

Figure 6A:
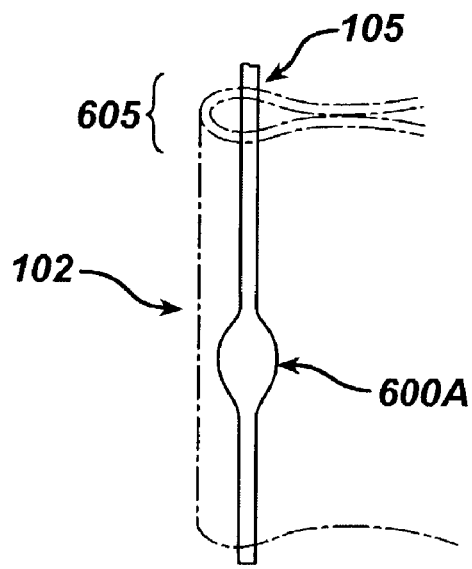
FIG. 6A is a perspective view illustrating a membrane limiting means according to one embodiment of the present invention.
Figure 6B:
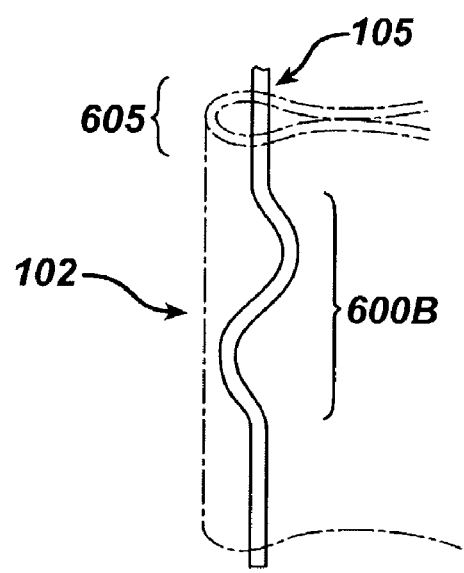
FIG. 6B is a perspective view illustrating a membrane limiting means according to one embodiment of the present invention.
Figure 6C:
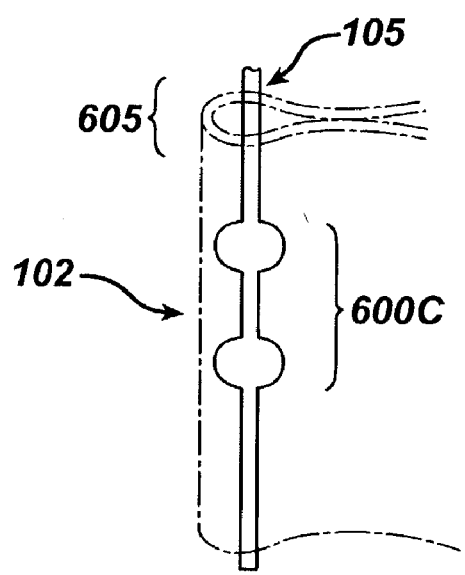
FIG. 6C is a perspective view illustrating a membrane limiting means according to one embodiment of the present invention.

In some applications, excessive sliding movement of the membrane assembly 102 is undesirable. In these embodiments, a limiting means may be integrated into the prosthetic valve 100 to limit the sliding movement of the membrane assembly 102. Examples of limiting means are shown in FIGS. 6A to 6C. In each embodiment a stop 600 (illustrated as stop 600A, 600B, and 600C in FIGS. 6A to 6C respectively) is integrated into the connecting member 105. The membrane assembly 102 is wrapped around the connecting member 105 and bonded to itself to form a loop collar 605. The loop collar 605 must be sized to inhibit the distal end 402 of the membrane assembly 102 from sliding past the stop 600. In FIG. 6A, the connecting member 105 has a thickened or "bulbous" section forming stop 600A. FIG. 6B illustrates an undulating stop 600B configuration. Similarly, FIG. 6C shows the stop 600C configured as a double bulbous section. It should be noted that the various configurations illustrated in FIGS. 6A through 6C are exemplary. One of ordinary skill in the art would understand that other configurations of stops may used.

In one embodiment of the invention the tubular membrane 400 is manufactured from a fiber reinforced elastomer, such as an elastomeric fluoropolymer. The elastomer allows the tubular membrane 400 to be extremely thin and elastic, while the fiber provides the necessary strength. One method used to produce this type of reinforced membrane valve is an Electro-Static Spinning (ESS) process.

The ESS process can be used to form a tubular membrane on many different types of structural frames, including frames associated with stents, stent grafts, valves, including percutaneously delivered venous valve, AAA (Abdominal Aortic Aneurysm) devices, local drug delivery devices, and the like. The disclosure of the ESS process for forming the tubular membrane 400 on the structural frame of a stent-based venous valve is exemplary, and thus not meant to limit the scope of this invention.

Figure 7:
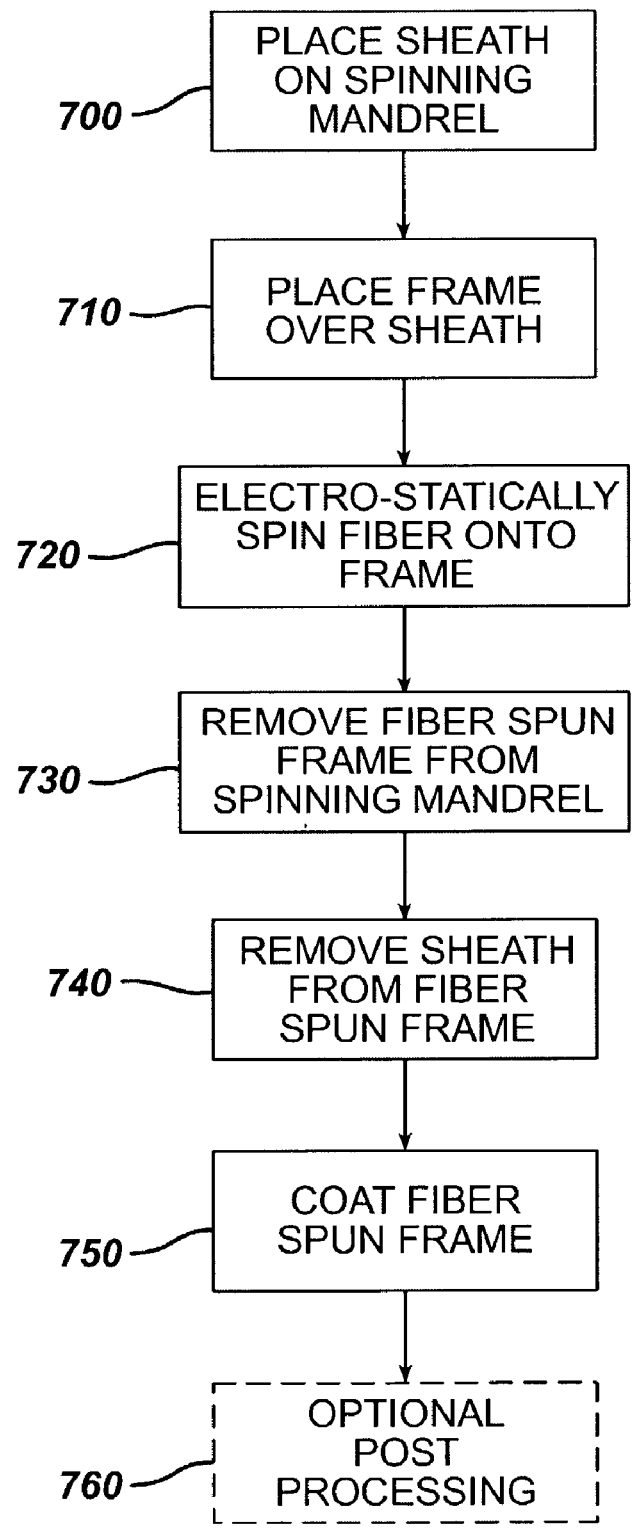
FIG. 7 is a flow diagram illustrating the steps to electrostatically spin a tubular membrane on a structural frame according to one embodiment of the present invention.

FIG. 7 shows the steps for electro-statically spinning a reinforced tubular membrane onto a structural frame according to one embodiment of the present invention. The ESS process comprises first placing a transfer sheath over a spinning mandrel as shown in step 700. The transfer sheath is a thin material that is used to prevent the ESS spun fiber from adhering to the mandrel. In instances where the mandrel itself is not electrically conducting, the transfer sheet may also provide the necessary electrical conductivity to attract the ESS spun fiber.

In one embodiment of the invention, the transfer sheath comprises a thin polymer tube, preferably fluoropolymer, of such a thickness that it can be easily deformed, and preferably collapsed, so that it is capable of being withdrawn conveniently from the lumen of the structural frame 101 and/or membrane tubular structure 400. The use of a transfer sheath made of other fibrous or sheet materials, such as other polymer, polymeric or metallic materials is not excluded.

Most preferably, the transfer sheath will be made of an ePTFE tube.

To enhance electrical conductivity and reduce the time it takes to build up the ESS layer, the ePTFE tube may be first coated with gold on at least a portion of the interior surface before placing the tube on the mandrel. This process may be completed by coating the inside of the tube, but is preferably done by coating the exterior of the ePTFE tube and then inverting the tube so that the gold coating is on the interior surface. The process may also be completed by inverting the tube so that the interior surface to be coated is exposed on exterior of the tube, coating the now exposed interior surface, and the inverting the tube so that the interior coated surface is back on the inside of the tube.

It should be noted that under certain circumstances it may not be necessary to use the transfer sheath. Such circumstances may include, for example, where the spinning mandrel is electro-statically conducting and has a surface or surface treatment that will prevent the ESS spun fiber from adhering to the mandrel.

In a preferred embodiment, the spinning mandrel is electrically conducting, and more preferably, is a metal coated with Teflon®. However, electrical conduction may not be essential. In such embodiments the spinning mandrel may be of any suitable material, including plastic material. Non-conductors may be used so long as the charge is capable of being transferred (i.e. bleed off) onto the transfer sheet or through the material itself.

The spinning mandrel may be hollow or solid, and preferably has a smooth surface to facilitate sliding between the transfer sheath and mandrel during removal. However, it may be desirable to maintain some degree of frictional resistance between the transfer sheath and mandrel to reduce slippage between the two components during the ESS process.

The valve structural frame 101 is then placed on the transfer sheath, step 710, and the ESS fiber is spun directly onto the valve structural frame 101 as shown in step 720. Preferably, the structural frame 101 is configured in the expanded or deployed state prior to placing the structural frame 101 on the spinning mandrel. This is generally the case when the structural frame 101 is of the self-expanding design. In other embodiments, such as balloon-expandable designs, the expansion mechanism may be integrated within the spinning mandrel to expand the structural frame during the spinning process.

The expandable mandrel may also be used for electro-statically spinning a fiber onto a self-expanding structural frame 101. In such instances, the self-expanding structural frame 101 is placed on the spinning mandrel in the expanded state, and the expansion mechanism on the expandable mandrel is mandrel activated to further radially expand the structural frame to a "super-expanded" state. ESS fiber is then spun directly onto the super-expanded structural frame 101. The larger diameter of the super-expanded structural frame 101 allows more material to be deposited on the structural frame, which may result in less post processing procedures. Post processing is described in step 760.

Electro-static spinning of a fiber is generally known in the art, and typically involves creating an electrical potential between a source component, i.e. the fiber or preferably a fiber forming liquid, and a downstream component, i.e. the spinning mandrel, transfer sheath or structural frame. The electrical potential causes the source component, typically the fiber forming liquid, to be attracted to, and thus move towards, the downstream component.

The electrical potential is created by providing an electrical charge to either the source or downstream component, and grounding the other component. Preferably, the source component will receive an electrical charge, while the downstream component is grounded.

Many different methods are known in the art for producing an electrical charge on a source component. In one embodiment, a fiber forming liquid is introduced into an electric field, whereby the fiber forming liquid is caused to produce a charged fiber. In another, more preferred embodiment, a device (introducer device) introducing the fiber forming liquid into the process is electrically charged, thus causing the fiber forming liquid to assume a like charge.

Several methods may be used to introduce the fiber forming liquid into the process, including spraying the fiber forming liquid from a nozzle, or injecting the fiber forming liquid from a needle, orifice or drip tube. In a preferred embodiment, the fiber forming liquid is sufficiently viscous to be extruded into the process with an extrusion device.

Once the fiber forming liquid is introduced into the process, it is hardened to form the ESS fiber. Hardening of the liquid into an ESS fiber may be accomplished, for example, by cooling the liquid until the fiber forming liquid will not lose its fibrous shape. Other methods for hardening the fiber may also include hardening by introducing a chemical hardener into the fiber forming liquid, or directing an air stream over the electrically drawn fiber forming liquid stream. In a preferred embodiment, a polymer is put into solution with a solvent to form a viscous fiber forming liquid. As the fiber forming liquid is drawn from the introducer device, the solvent comes out of solution forming the polymer fiber.

Various drying techniques may be applied to evaporate the solvent and bring the polymer out of solutions. Drying techniques may include, for example, applying heat or airflow to or over the coated fiber spun frame assembly. In addition, the solvent may dry naturally without applying artificial drying techniques.

The viscosity of the fiber forming liquid may be adjusted based on the material used for the source component, and the percent solids desired as the source component reaches the downstream component. Typical concentrations range from 2 to 100 percent. The choice of concentration depends on the material, its molecular weight, the solvent efficiency, and temperature. The concentration and temperature also control the diameter of the fiber. These viscosities will typically produce a fiber at the downstream component having percent solids in the range of about 95 percent to about 100 percent, and preferably over 99 percent. This is desirable in order to produce structures that contain entangled or point bonded fibers. Concentrations lower than 95 percent can be used if it is desired to allow filaments to fuse together into a sheet-like barrier structure.

The hardened fiber is then collected onto the structural frame. Collecting of the fiber involves attracting the ESS fiber to the downstream component (i.e. spinning mandrel, transfer sheath or structural frame) of the ESS system, while spinning the downstream component. In a preferred embodiment, where the source component is electrically charged, a downstream component is grounded to complete the electric potential between the source and downstream component, and thus attract the ESS fiber. In other embodiments, a downstream component may be electrically charged to attract the ESS fiber where the source component is grounded. In still other embodiments, various combinations of downstream components may be electrically charged to enhance electrical conductivity and reduce the time it takes to build up the ESS layer.

Particular ESS fibers suitable for this spinning process include fluoropolymers, such as a crystalline fluoropolymer with an 85/15% (weight/weight ratio) of vinylidene fluoride/hexafluoropropylene (VDF/HFP). Solvay Solef® 21508 and Kynarflex 2750-01 are two such examples. However, one of skill in the art would understand that any material possessing the desired characteristics may be used, including, for example: bioabsorbable polymers, such as polyglycolic acid, polylactic acid, poly (paradioxanone), polycaprolactone, poly (trimethylenecarbonate) and their copolymers; and semicrystalline bioelastomers, such as 60/40% (weight/weight ratio) of polylactic acid/polycaprolactone (PLA/PCL), 65/35 (weight/weight ratio) of polyglycolic acid/polycaprolactone (PGA/PCL), or nonabsorbable siliconized polyurethane, non-siliconized polyurethanes, siliconized polyureaurethane, including siliconized polyureaurethane end capped with silicone or fluorine end groups, or natural polymers in combination thereof. It should be noted that poly(trimethylenecarbonate) can not be spun as a homopolymer.

The spinning process should be continued until an ESS fiber tube, or fabric, is formed having a wall thickness of between 5 μm and 100 μm or more, preferably, approximately 20 μm. The ESS fiber spun structural frame 101 is then removed from the spinning mandrel, step 730, before the transfer sheath is removed from the fiber spun frame, step 740. Once this step is completed, the fiber spun structural frame is coated in a solution of polymer, such as fluoroelastomer, as shown in step 750.

Several different methods may be utilized to perform the coating process on the fiber spun structural frame, including spray coating with an air or airless sprayer, dip coating, chemical vapor deposition, plasma coating, co-extrusion coating, spin coating and insert molding. In still another preferred embodiment, the fiber spun structural frame is first dip coated in a polymer solution, and then spun about its longitudinal axis to more evenly distribute the coating. In this embodiment, the fiber spun structural frame is not first removed from the spinning mandrel. Instead, the frame/mandrel assembly is dip coated and spun before removing the fiber spun structural frame from the spinning mandrel. Still other methods for coating the fiber spun structural frame would be obvious to one of skill in the art.

The coating process may act to encapsulate and attach at least a portion of the spun ESS reinforcement fiber to the structural frame 101. It should be noted that it in some embodiments of the invention, some movement between the membrane assembly 102 and the structural frame 101 is desired. Accordingly, not all of the ESS fiber spun structural frame may be coated.

The coating process may also remove some porosity of the membrane material. However, it may be desirable to maintain some porosity in particular embodiments to promote biological cell grown on and within the membrane tubular structure.

The coating solution preferably comprises a polymer put into solution with a solvent. As the solvent evaporates, the polymer comes out of solution forming the coating layer. Accordingly, for the process to work properly, the solvent used in the coating solution should not dissolve or alter the ESS fibers being coated. By way of example, a coating solution of 60/40% VDF/HFP in methanol (methanol being the solvent) has been found to be a suitable solution for coating an ESS fiber comprised of 85/15% VDF/HFP.

In one embodiment of the invention, the polymer comprising the coating is Daikin's Dai-El G701BP, which is a 60/40% VDF/HFP. In addition, Daikin's Dai-El T630, a thermoplastic elastomer based on vinylidene fluoride/hexafluoropropylene/tetrafluoroethylene (VDF/HFP/TFE) can also be used. Again, one of ordinary skill in the art would understand that other materials having suitable characteristics may be used for the coating, for example, other polymers, such as siliconized polyurethane, including Polymer Technology Group's Pursil, Carbosil, Purspan and Purspan F.

The coating process may be repeated until the desired characteristics and thickness are achieved. For venous valves a thickness of between 12 μm and 100 μm and preferably between 25 μm and 50 μm has been found to be acceptable.

Once the coating process is complete some post processing of the membrane tubular structure 400 may take place to achieve particular desired characteristics or configurations. This may include creating the final form of the membrane assembly 102. The post processing step is shown as optional step 760 in FIG. 7.

The post processing step 760 may be used to form or shape, for example, a valve cusp, similar to cusp 404, in the membrane tubular structure 400. In addition, post processing may change the characteristics of the membrane tubular structure 400 by thickening or thinning the membrane in particular locations. Thickening the membrane may add rigidity and reinforcement to a particular area. Thinning the membrane may make the membrane more pliable, which is a desirable characteristic for the valve flaps 403. Still other post processing procedures may change the physical shape of the membrane tubular structure 400, for example, by forming the loop collar 605 along the distal edge of membrane tubular structure 400. The loop collar 605 may assist in controlling the movement (translational and circumferential) of the membrane assembly 102 along the connecting members 105. The loop collars 605 may also reduce fatigue and tear stresses in the membrane.

Figure 8A:
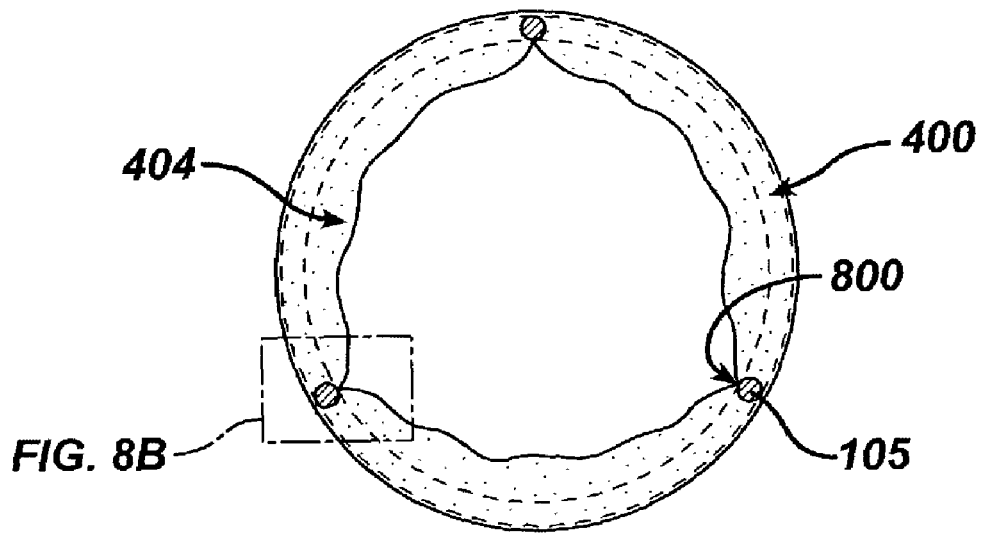
FIG. 8A is section view illustrating the expanded (deployed) prosthetic venous valve assembly in the open position after some post processing according to one embodiment of the present invention.
Figure 8B:
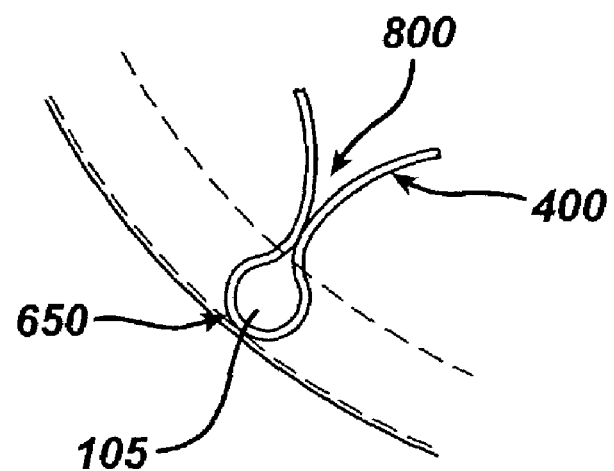
FIG. 8B shows a close-up section view illustrating a portion of the valve assembly after some post processing according to one embodiment of the present invention.

FIGS. 8A and 8B show an example of the result of a post processing step that forms a loop collar 605 according to one embodiment of the present invention. To achieve this result, the membrane tubular structure 400 is wrapped around at least one element of structural frame 101 (connecting member 105) and bonded to itself at bond point 800.

Figure 9:
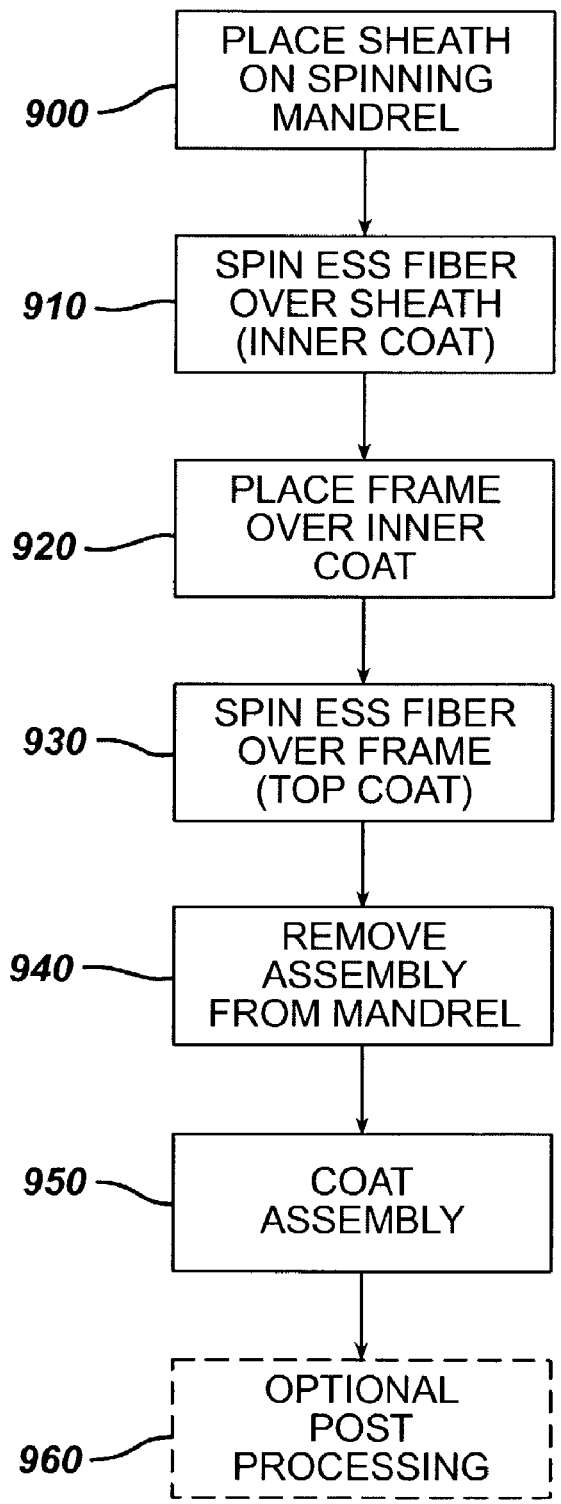
FIG. 9 is a flow diagram illustrating the steps to electrostatically spin a tubular membrane on a structural frame according to one embodiment of the present invention.

Another method for electro-statically spinning a tubular membrane onto a radially expandable structural frame according to another embodiment of the present invention is shown in FIG. 9. Although similar to the process described above, this alternative method provides an ESS spun membrane on the inside, as well as the outside of the structural frame. The inner and outer ESS spun membranes may mechanically adhere to each other, and in a sense encapsulated the structural frame. This configuration provides some additional features, including having a smoother interior surface that reduces turbulence, improves flow dynamics and lowers the chance of thrombosis formation.

Similar to the embodiment described earlier, the ESS process comprises first placing a transfer sheath over a spinning mandrel as shown in step 900. It should be noted that under certain circumstances it may not be necessary to use the transfer sheath. Such circumstances may include, for example, where the spinning mandrel is electro-statically conducting and has a surface or surface treatment that will prevent the ESS spun fiber from adhering to the mandrel.

An ESS fiber is then spun directly onto the transfer sheath creating an inner coat membrane as shown in step 910. The ESS process should continue until an ESS tube is formed having a wall thickness of between 2 µm and 50 µm or more, and preferably, approximately 20 µm. As previously stated, the inner coat membrane covers some or all of the interior surface of structural frame 101. The structural frame 101 is then radially expanded and placed over the inner coat membrane on the spinning mandrel as shown in step 920. Expansion of the structural frame 101 may be achieved by several different methods. One method includes taking advantage of the thermal and shape memory characteristics of particular materials. For example, shape memory materials, such as Nitinol, possess little or no recoil ability when cooled, but exhibit a high degree of memory, i.e. the ability to return to a configured shape, when heated. Cooling the Nitinol structural frame 101 before expansion allows the structural frame to remain in the expanded configuration until being heated. Accordingly, the Nitinol structural frame 101 can be cooled, expanded, and then placed over the inner coat membrane. Once in place, the structural frame can be heated to activate the Nitinol memory characteristics, causing the Nitinol structural frame 101 to contract to the pre-expansion size and configuration.

The structural frame 101 is sized such that when configured in the expanded or deployed state, it will fit tightly over the inner coat membrane on the spinning mandrel. To fit the structural frame 101 over the inner coat membrane, the structural frame 101 may have to be radially expanded ("super-expanded") to a diameter slightly larger than the expanded deployed state to allow the structural frame 101 to fit over the inner coat membrane.

Once the structural frame 101 is placed over the inner coat membrane, another ESS fiber is spun directly onto the structural frame, as shown in step 930, to form a top-coat membrane. The ESS process should continue until the top-coat membrane tube is formed having a wall thickness of between 2 µm and 50 µm or more, and preferably, approximately 20 µm. The top-coat membrane may cover and adhere to the inner coat membrane through the interstitial spaces between the elements that comprise the structural frame 101.

As stated in an earlier described embodiment of the invention, the structural frame 101 is configured on the mandrel in the expanded deployed state prior to spinning the top-coat membrane. In other embodiments, it may be desirable to expand (super expand) the structural frame 101 on the spinning mandrel during or prior to the spinning process. This procedure may alter the configuration and properties of the spun membrane, resulting in less post processing of the membrane. Post processing is described in step 960.

The structural frame 101, with the inner coat and top coat membranes, is then removed from the spinning mandrel, as shown in step 940, and coated with a solution of highly elastic polymer as shown in step 950. As stated previously, the coating process may be achieved using several different coating methods, including spin coating, spray coating, dip coating, chemical vapor deposition, plasma coating, co-extrusion coating and insert molding.

As previously described, a representative elastomeric polymer is a fluoroelastomer. The coating process may be repeated until the desired characteristics and thickness are achieved. For a venous valve application, a thickness of between 12 µm and 100 µm, and preferably between 25 µm and 50 µm, has been found to be acceptable.

Once the coating process is complete, some post processing of the tubular membrane may take place, as shown as an optional step 960 in FIG. 9.

Although each of the above described ESS methods spin the fiber directly on to the structural frame, one of ordinary skill in the art would understand that a tubular membrane may also be spun separately, and then placed over the structural frame 101 by known methods.

Figure 10:
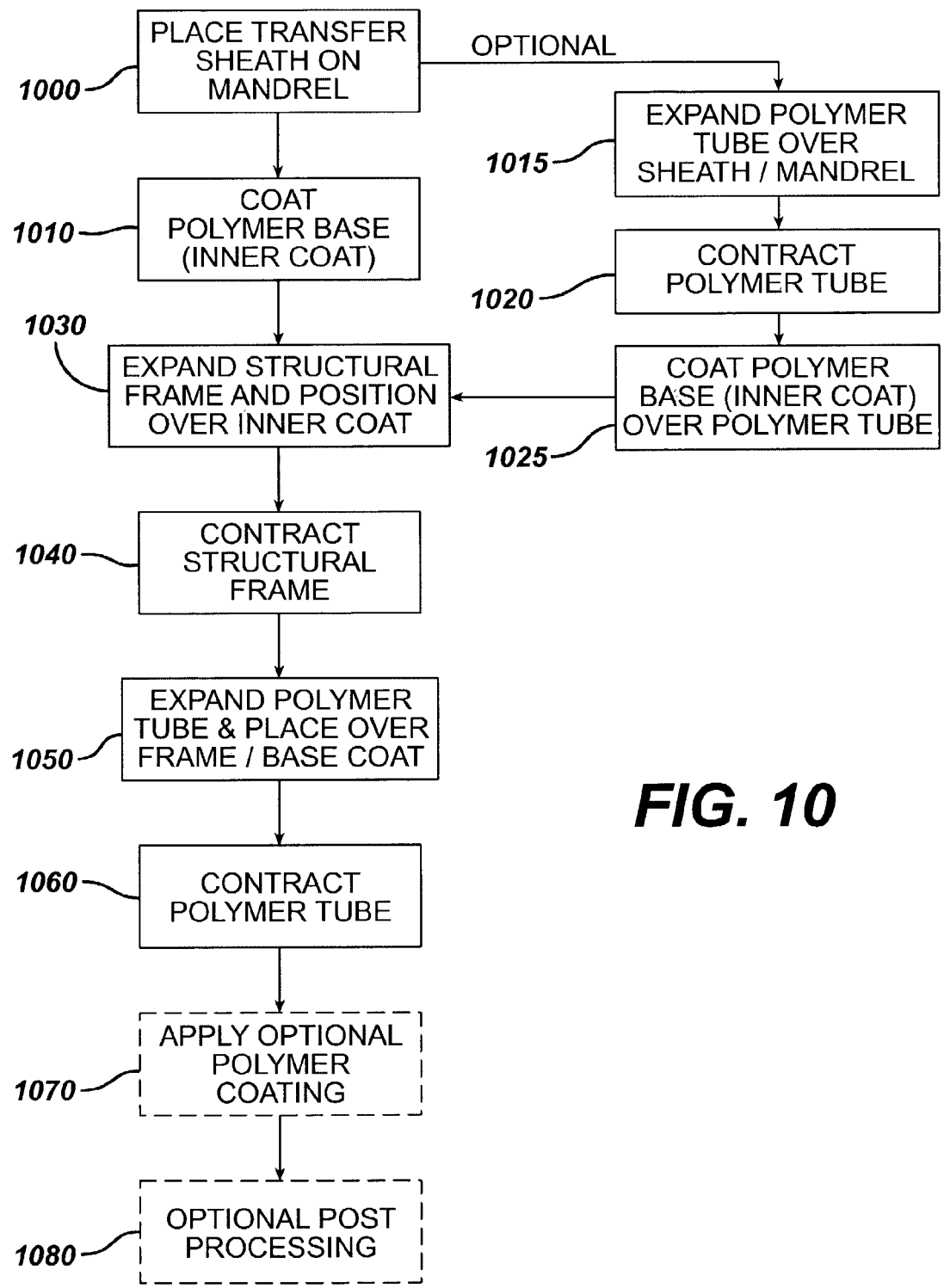
FIG. 10 is a flow diagram illustrating the steps to place a tubular membrane over a structural frame according to one embodiment of the present invention.

Another, more preferred method for forming the membrane material over and around the structural frame 101 is shown in FIG. 10. As described earlier, this method is presented in the context of a prosthetic valve application. However, the method may be applied generally to any application where a micro-cellular foam or pourous material, particularly an ePTFE membrane, needs to be placed over and around a radially expandable structural frame. Exemplary structural frames may include stents, stents grafts, valves (including percutaneously delivered venous valves), AAA (Abdominal Aortic Aneurysm) devices, local drug delivery devices, and the like. Accordingly, the disclosed device is not meant to limit the scope of the inventive method.

In this embodiment, a tubular structure is fabricated from a polymer material that can be processed such that it exhibits an expanded cellular structure, preferably expanded Polytetrafluoroethylene (ePTFE). The ePTFE tubing is made by expanding Polytetrafluoroethylene (PTFE) tubing, under controlled conditions, as is well known in the art. This process alters the physical properties that make it satisfactory for use in medical devices. However, one of ordinary skill in the art would understand that other materials that possess the necessary characteristics could also be used.

The method comprises first placing a transfer sheath over a mandrel as shown in step 1000. As described earlier, the transfer sheath is a thin material that is used to prevent the tubing and coating from adhering to the mandrel. The transfer sheath may be made of sheet metal, metal foil, or polymer sheet, such as for example Polytetrafluoroethylene (PTFE). Preferably, the transfer sheath will be made of a material that can be easily deformed, and preferably collapsed so that it can be withdrawn conveniently from the lumen of the tube once the process is complete.

The transfer sheath/mandrel combination are then coated in a solution of highly elastic polymer, such as fluoroelastomer, as shown in step 1010, to form an inner membrane. As stated previously, the coating may be applied using various methods, including, for example, spin coating, spray coating, dip coating, chemical vapor deposition, plasma coating, co-extrusion coating and insert molding.

In one embodiment of the invention, the coating solution comprises a polymer put into solution with a solvent, such as methanol. In addition, most solvents can be used with expanded Polytetrafluoroethylene (ePTFE).

In a preferred embodiment of the invention, the polymer comprising the coating includes Daikin's Dai-El T630, a thermoplastic elastomer based on vinylidene fluoride/hexafluoropropylene/tetrafluoroethylene (VDF/HFP/TFE) and blends thereof. Other preferred polymers include siliconized polyurethanes, including silicone-urethane copolymers, and blends thereof. Silicone-urethane copolymers can consist of segmented polyetherurethane with aromatic urea as hard segments and poly (tetramethyleneoxide) [PTMO] as soft segments. Silicone (20 to 25%) is added by replacing PTMO with polydimethylsiloxane, and fluorine (0.5 to 2%) can be added by surface-modifying end groups. Again, one of ordinary skill in the art would understand that other materials having suitable characteristics may be used for the coating, for example, other polymers and blends thereof. Preferred siliconized polyurethanes include Polymer Technology Group's Pursil, Carbosil, Purspan and Purspan F.

The coating process should continue until the inner membrane achieves a wall thickness of between 6 μm and 100 μm or more, preferably between 12 μm to 25 μm.

In an alternate embodiment, a polymer tube, preferably an ePTFE tube, may be expanded and placed over the sheath/ mandrel combination (step 1015), before being contracted (step 1020). Expansion may be by any suitable expansion means known in the art, including mechanical expansion, such as by means of a balloon expansion device or expandable cage, expansion by utilizing a tapered mandrel (i.e. sliding the polymer tube over a tapered mandrel of increasing diameter), etc. In addition other means may be used in conjunction with the expansion means to assist placing the tube over the sheath mandrel combination. These assist means may include, for example, thermally expanding the tube with heat, or chemically expanding the tube with a solvent. These methods are known in the art.

Contraction of the tube is typically done by reversing the method used to expand the tube. For example, ePTFE is naturally elastic. If the ePTFE tube was expanded by a mechanical expansion means, removing the expansion means would allow the ePTFE tube to contract towards it pre-expansion configuration. In addition the contraction of the tube may be enhanced by applying heat or chemicals (solvents).

Once the tube is expanded over the sheath/mandrel, the whole assembly may be coated with a solution of highly elastic polymer, such as fluoroelastomer as shown in step 1025 to form the inner membrane. The coating process is similar to that shown in step 1010 above, and may be achieved by any method known in the art capable of achieving the desired result, including spin coating, spray coating, dip coating, chemical vapor deposition, plasma coating, co-extrusion coating and insert molding.

The coating process described in step 1025 should continue until the inner membrane described in the alternate embodiment is coated with a polymer base having a wall thickness of between 6 μm and 100 μm or more, preferably between 12 μm to 25 μm.

The structural frame 101 is then radially expanded and positioned over the inner membrane as shown in step 1030. The structural frame 101 may be radially expanded using any know expansion means, including a balloon expansion device or frame expansion device. In one embodiment of the invention, the structural frame 101 is constructed from a shape memory alloy, such as Nitinol. As previously described, Nitinol characteristically holds a deformed shaped when cooled, and returns to its original shape when heated. Accordingly, it is possible to hold a Nitinol structural frame 101 in the radially expanded state by cooling the frame before the expansion means is removed. This will facilitate placement of the Nitinol structural frame over the inner membrane.

The structural frame 101 may then be radially contracted over the inner membrane, as shown in step 1040. It is desirable to maintain a slight interference fit between the structural frame 101 and the inner membrane. The method to radially contract the structural frame 101 may depend on the material and type of construction of the structural frame 101, and is not meant to limit the scope of the invention. As described above, a structural frame 101 constructed from a shape memory alloy, such as Nitinol, can be radially contracted (to the pre-expanded and cooled size) by heating. Depending on the material used, other methods that may also be employed to radially contract the structural frame include, simply removing the expansion means providing the radial expansion force, or applying a compressive force about the structural frame 101. Still other methods to radially contract the structural frame 101 would be obvious to one of skill in the art.

Once the structural frame 101 is contracted over the inner membrane, a second polymer tube, preferably an ePTFE tube, is expanded and placed over the structural frame, as shown in step 1050, forming an outer membrane. The tube is then contracted into position as shown in step 1060. As described earlier, the tube may be expanded by several different means, including mechanical, thermal, or chemical (solvents) expansion. Similarly, contraction of the tube may be accomplished by the methods described in step 1020.

In embodiments where two separate ePTFE tubes are used for the inner and outer membranes, as described in steps 1015 and 1050 respectively, each tube should have a wall thickness of between 25 μm and 50 μm before expansion; yielding a wall thickness of between 6 μm and 10 μm after expansion and placement. It should be noted that these membranes may or may not be bonded together. If only a single ePTFE tube is used for the outer membrane only, as described in step 1050 (not following alternate steps 1015 through 1025), the tube should have a wall thickness before expansion of between 50 μm and 100 μm; yielding a wall thickness after expansion of between 12 μm and 20 μm.

The inner and outer membranes combine to for a membrane structure. In the valve example described above, the membrane structure would represent membrane tubular structure 400, while the structural frame would represent the structural frame 101.

Once the membrane structure is formed, some or all of the assembly may be optionally coated with a solution of a highly elastic polymer, such as an elastomeric polymer, as shown in step 1070. The coating may be applied by any method known in the art, including spin coating, spray coating, dip coating, chemical vapor deposition, plasma coating, co-extrusion coating and insert molding.

As described earlier (see step 1010) the coating solution may be a fluoroelastomer. In one embodiment of the invention, the coating is Daikin Dai-El T630, a thermoplastic elastomer based on vinylidene fluoride/hexafluoropropylene/tetrafluoroethylene (VDF/HFP/TFE) and blends thereof. Again, one of ordinary skill in the art would understand that other materials having suitable characteristics might be used for the coating, for example, other polymers, such as siliconized polyurethane.

The coating process should continue until the coating achieves a wall thickness of between 6 μm and 100 μm or more, preferably between 12 μm to 25 μm.

Once the coating process is complete, some post processing of the membrane structure may take place to achieve particular desired characteristics or configurations. This post processing step is shown as optional step 1080 in FIG. 10.

By way of example, for valve applications, the post processing step 1080 may be used to form or shape valve cusps, similar to cusps 404, or valve flaps, such as flaps 403, in the membrane structure. In addition, post processing may change the characteristics of the membrane structure by thickening or thinning the membrane in particular locations. Thickening the membrane may add rigidity and reinforcement to a particular area. Thinning the membrane may make the membrane more pliable. Still other post processing procedures may change the physical shape of the membrane structure, for example, by forming the loop collar 605 along the distal edge of membrane assembly 102. The loop collar 605 may assist in controlling the translational and circumferential movement of the membrane assembly 102 along the connecting members 105. The loop collars 605 may also reduce fatigue and tear stresses in the membrane.

It is important to note that the local delivery of drug/drug combinations may be utilized to treat a wide variety of conditions utilizing any number of medical devices, or to enhance the function and/or life of the device. Medical devices that may benefit from this treatment include, for example, the frame based unidirectional flow prosthetic implant subject of the present invention.

Accordingly, in addition to the embodiments described above, therapeutic or pharmaceutic agents may be added to any component of the device during fabrication, including, for example, the ESS fiber, polymer or coating solution, membrane tube, structural frame or inner and outer membrane, to treat any number of conditions. In addition, therapeutic or pharmaceutic agents may be applied to the device, such as in the form of a drug or drug eluting layer, or surface treatment after the device has been formed. In a preferred embodiment, the therapeutic and pharmaceutic agents may include any one or more of the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) ll$_b$/lll$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As earlier disclosed, the present invention relates to a medical device, particularly a stent-based valve, to be delivered and deployed in a body lumen or vessel. One typical use of this disclosed stent-based valve is to assist or replace insufficient venous valves in the vascular system.

Figure 11:
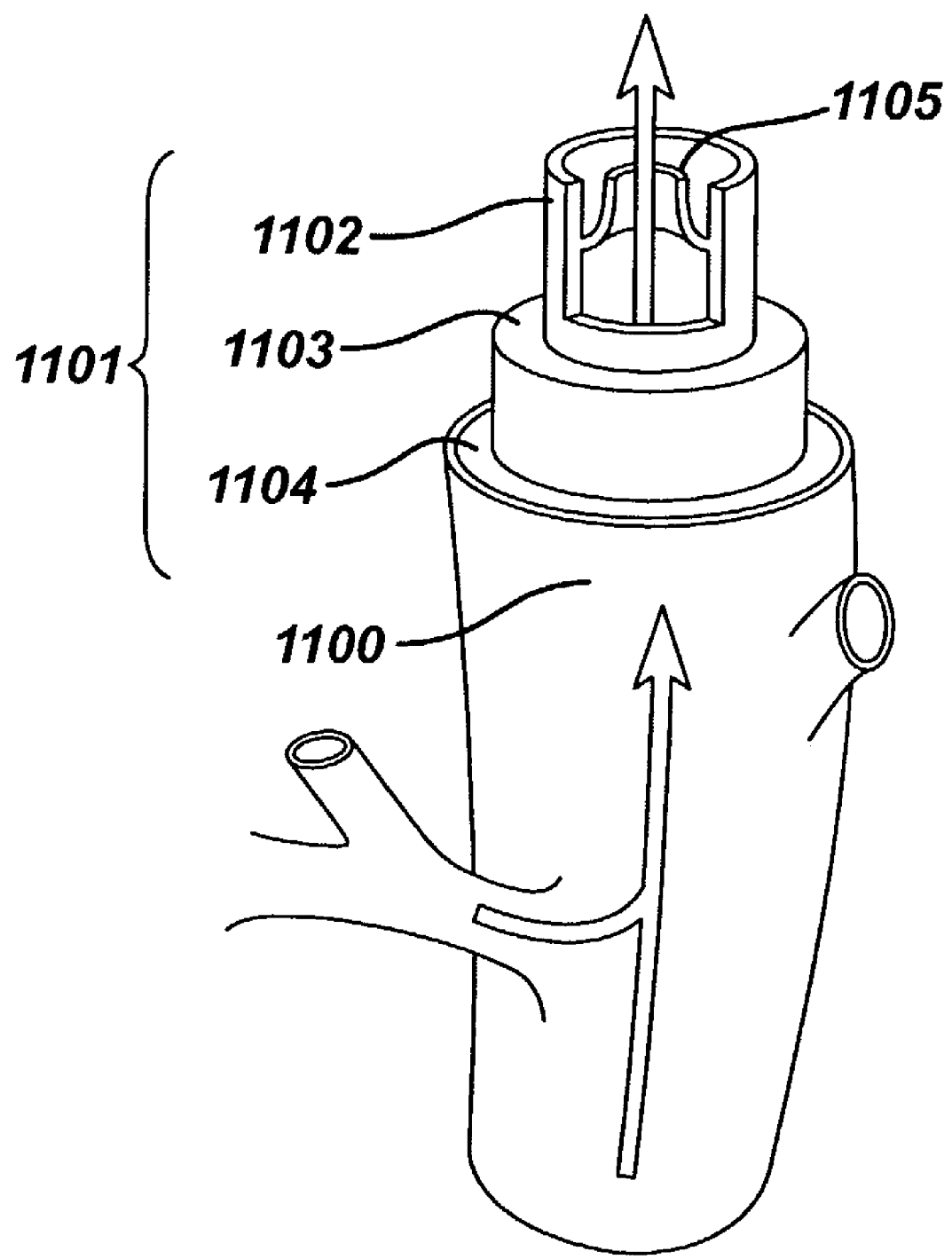
FIG. 11 illustrates a sectioned view of a typical vein.

A sectioned view of a typical vein is illustrated in FIG. 11. The vein 1100 may be any of the tubular branching vessels that carry blood from the capillaries toward the heart (antegrade blood flow). Vein 1100 comprises a vein wall 1101 formed of three layers.

The innermost layer of the vein wall 1101 is the Tunica Intima 1102. The Intima 1102 is a simple epithelium made up of a single layer of flat epithelial cells comprising connective and elastic tissue. The second and main portion of the vein wall 1101 is the Tunica Media 1103. The Media 1103 is made up of a combination of smooth muscle and elastic tissue. The smooth muscle portion of the Media 1103 is usually larger than the other layers and consequently provides support to counteract outward radial force caused by blood pressure within the vessel. To some extent, the Media 1103 also provides support against the radial expansion of the prosthetic venous valve 100. Finally, the third layer of the vein wall 1101 is the outer surface or the Tunica Adventitia 1104. The Adventitia 1104 is comprised generally of connective tissue, but may also include arties and veins that supply the tissues of the vessel.

In addition, veins greater than approximately two (2) millimeters in diameter located below the heart often have one or more natural valves 1105 at intervals to prevent reflux of the blood (retrograde blood flow). These venous valves 1105 are necessary to counteract the effect of gravitation force on antegrade blood flow.

When the prosthetic venous valve 100 of the present invention is deployed into position, the proximal and distal anchors 103, 104 expand into the vein wall 1101, and engage the Tunica Intima 1102. A transverse cross-sectional view of an open prosthetic venous valve 100 deployed into vein 1100 during antegrade blood flow is shown in FIG. 12.

The correct placement of the anchors 103, 104 may result in mounds of tissue 1200 protruding between the strut members comprising the distal anchor 104 after the anchor 104 has been embedded in the Tunica Intima 1102. These tissue mounts 1200 retain endothelial cells that can provide for the re-endothelialization of the vessel wall. Endothelial regeneration of the vessel wall may cause endothelial cells to migrate to, and over the anchor 104 members, resulting in a thin tissue layer encapsulating the anchor 104 struts. This endothelialization may assist in anchoring the prosthetic venous valve 100 in place.

Continued tissue growth or neointima and/or intimal hyperplasia through the openings of the expanded structural frame 101 meshes as a result of tissue injury may cause vessel restenosis. As described earlier, to deter or control neointimal hyperplasia, the structural frame 101 may be coated or treated with a therapeutic or pharmaceutic agent, such as an anti-restenotic (antiproliferative). Similarly, the membrane assembly 102 may be coated or impregnated with a therapeutic or pharmaceutic agent.

Figure 12:
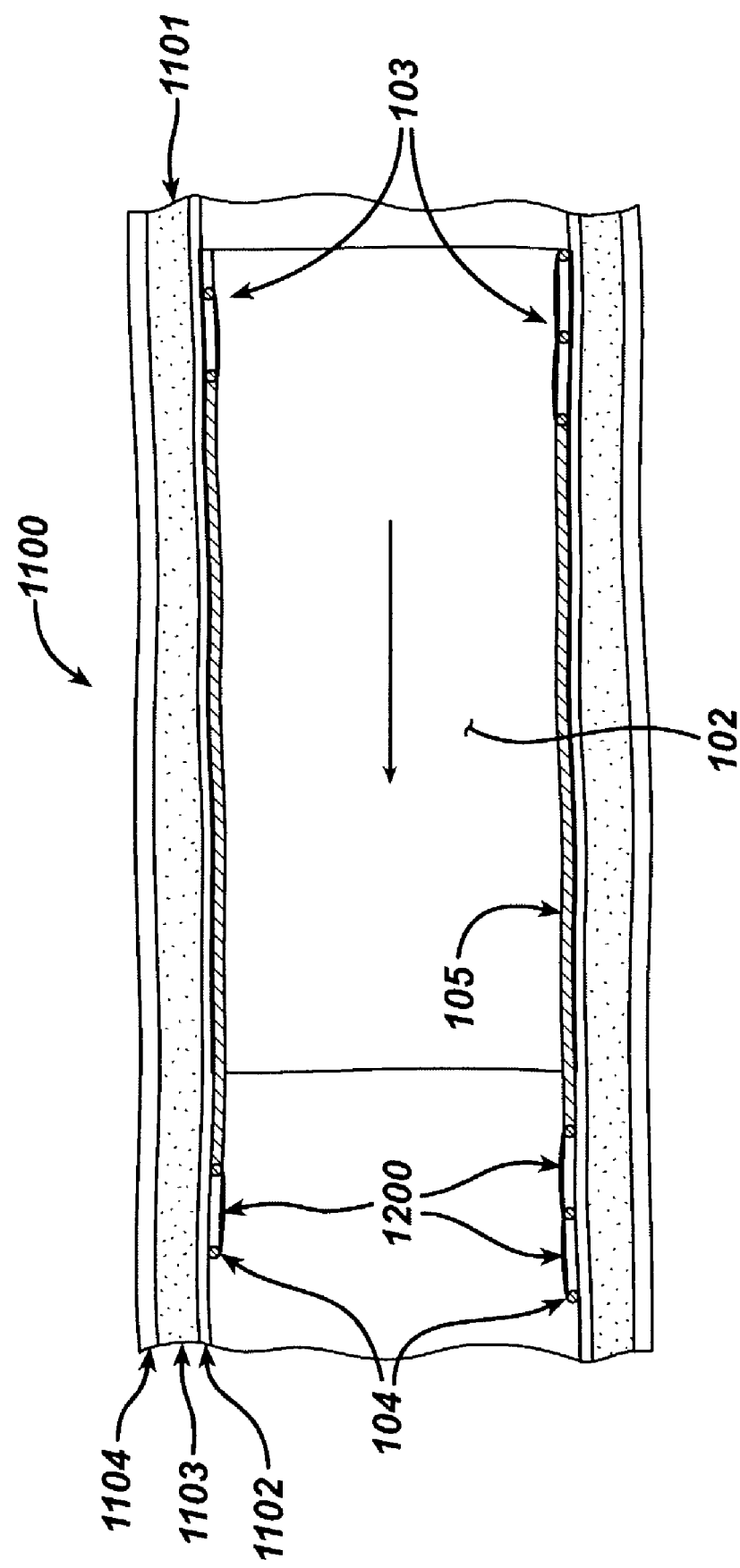
FIG. 12 shows a transverse cross-sectional view of the vein and deployed prosthetic venous valve according to one embodiment of the present invention.

The embodiment illustrated in FIG. 12 depicts the biocompatible membrane assembly 102 located on the exterior surface of the proximal anchor 103 and connecting members 105. In this configuration, the correct placement of the proximal anchor 103 expands the exterior surface of the biocompatible membrane assembly 102 into the Tunica Intima 1102, creating a substantially fluid tight seal between the membrane assembly 102 and vein wall 1101. This sealing effect substantially eliminates blood flow around the exterior of the prosthetic venous valve 100. In addition, the sealing effect facilitates the membrane assembly 102 closing during retrograde blood flow.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be prosthetic "venous valves" may be modified to instead incorporate prosthetic "heart valves" and are also contemplated. Moreover, all assemblies described are believed useful when modified to treat other vessels or lumens in the body, in particular other regions of the body where fluid flow in a body vessel or lumen needs to be controlled or regulated. This may include, for example, the coronary, vascular, non-vascular and peripheral vessels and ducts. Accordingly, it should be understood that various applications, modifications and substitutions may be made of equivalents without departing from the spirit of the invention or the scope of the following claims.

The following claims are provided to illustrate examples of some beneficial aspects of the subject matter disclosed herein which are within the scope of the present invention.

What is claimed is:

1. A prosthetic valve comprising:
   a radially expandable structural frame including a proximal anchor and a distal anchor, the proximal and distal anchors being formed from a lattice of interconnected elements, and having a substantially cylindrical configurations with first and second open ends and a longitudinal axis extending there between;
   one or more connecting members, the one or more connecting members having a first and a second end, the first end of each connecting member being attached to the proximal anchor and the second end of each connecting member being attached to the distal anchor; and
   a tubular biocompatible membrane assembly attached to the abluminal surface of the proximal anchor and extending distally along the one or more connecting members, the biocompatible membrane assembly having proximal and distal ends, wherein the distal end of the biocompatible membrane assembly is engaged with an abluminal surface of the one or more connecting members whereupon terminating with supple valve flaps biased towards an open position.

2. The prosthetic valve of claim 1 wherein the structural frame is expandable by an expansion means.

3. The prosthetic valve of claim 2 wherein the expansion means is a balloon.

4. The prosthetic valve of claim 1 wherein the structural frame is self-expanding.

5. The prosthetic valve of claim 1 wherein the structural frame comprises a material selected from the group consisting of stainless steel, tantalum, platinum alloys, niobium alloy, cobalt alloy, and nickel-titanium alloy.

6. The prosthetic valve of claim 1 wherein the structural frame comprises a polymer.

7. The prosthetic valve of claim 1 wherein the one or more connecting members are substantially straight members oriented in a direction substantially parallel to the longitudinal axis.

8. The prosthetic valve of claim 1 wherein the one or more connecting members are helically shaped members oriented in a semi-spiral about the longitudinal axis.

9. The prosthetic valve of claim 1 wherein the one or more connecting members are biased inward toward the longitudinal axis.

10. The prosthetic valve of claim 1 wherein the lattice of interconnected elements comprises a plurality of longitudinally arranged strut members and a plurality of loop members connecting the adjacent strut members, each loop member having a substantially semi-circular configuration creating an inflection point with an inside and outside radii.

11. The prosthetic valve of claim 10 wherein the first end of the one or more connecting members is connected to the proximal anchor at the outside radii of the inflection point, and the second end of the one or more connecting members is connected to the distal anchor at the outside radii of the inflection point.

12. The prosthetic valve of claim 10 wherein the first end of the one or more connecting members is connected to the proximal anchor at the inside radii of the inflection point, and the second end of the one or more connecting members is connected to the distal anchor at the inside radii of the inflection point.

13. The prosthetic valve of claim 10 wherein the first end of the one or more connecting members is connected to the proximal anchor at the inside radii of the inflection point, and the second end of the one or more connecting members is connected to the distal anchor at the outside radii of the inflection point.

14. The prosthetic valve of claim 10 wherein the first end of the one or more connecting members is connected to the proximal anchor at the outside radii of the inflection point, and the second end of the one or more connecting members is connected to the distal anchor at the inside radii of the inflection point.

15. The prosthetic valve of claim 10 wherein the first end of the one or more connecting members is connected to the proximal anchor at the strut, and the second end of the one or more connecting members is connected to the distal anchor at the strut.

16. The prosthetic valve of claim 1 wherein the biocompatible membrane assembly is formed from a flexible membrane-like material.

17. The prosthetic valve of claim 16 wherein the membrane-like material is a biological material.

18. The prosthetic valve of claim 17 wherein the biological material is a vein.

19. The prosthetic valve of claim 16 wherein the membrane-like material is a synthetic material.

20. The prosthetic valve of claim 19 wherein the synthetic material is an elastomeric polymer.

21. The prosthetic valve of claim 19 wherein the synthetic material is a bioabsorbable material.

22. The prosthetic valve of claim 19 wherein the synthetic material further comprises a reinforcement fiber.

23. The prosthetic valve of claim 22 wherein the reinforcement fiber is formed directly on the radially expandable structural frame.

24. The prosthetic valve of claim 16 wherein the membrane-like material is in the form of a tube having a first end and a second end.

25. The prosthetic valve of claim 24 wherein the first end of the tube comprises one or more valve flaps.

26. The prosthetic valve of claim 24 wherein the first end of the tube is located between the proximal and distal anchors.

27. The prosthetic valve of claim 24 wherein the second end of the tube is located proximal to at least one half of the proximal anchor.

28. The prosthetic valve of claim 24 wherein the tube comprises one or more valve cusps.

29. The prosthetic valve of claim 1 wherein the biocompatible membrane assembly is fixedly attached to the proximal anchor.

30. The prosthetic valve of claim 29 wherein the attachment results from radial pressure of the proximal anchor against the biocompatible membrane assembly.

31. The prosthetic valve of claim 30 wherein the membrane assembly is attached by the use heat.

32. The prosthetic valve of claim 30 wherein the membrane assembly is attached by a chemical bond.

33. The prosthetic valve of claim 30 wherein the membrane assembly is attached by use of a mechanical means.

34. The prosthetic valve of claim 33 wherein the mechanical means includes welding.

35. The prosthetic valve of claim 33 wherein the mechanical means includes suturing.

36. The prosthetic valve of claim 29 wherein the membrane assembly is attached by use of a binder.

37. The prosthetic valve of claim 36 wherein the binder comprises a polymer.

38. The prosthetic valve of claim 37 wherein the binder comprises a polymer selected from the group consisting essentially of elastomeric polymer, siliconized polyurethane, polyurethane, and silicone.

39. The prosthetic valve of claim 1 wherein at least a portion of the structural frame is coated with an agent.

40. The prosthetic valve of claim 39 wherein the agent coating contains a therapeutic agent.

41. The prosthetic valve of claim 39 wherein the agent coating contains a pharmaceutic agent.

42. The prosthetic valve of claim 39 wherein the agent coating comprises an agent eluting layer.

43. The prosthetic valve of claim 1 wherein at least a portion of the biocompatible membrane assembly is coated with an agent.

44. The prosthetic valve of claim 43 wherein the agent coating contains a therapeutic agent.

45. The prosthetic valve of claim 43 wherein the agent coating contains a pharmaceutic agent.

46. The prosthetic valve of claim 43 wherein the agent coating comprising an agent eluting layer.

47. The prosthetic valve of claim 1 wherein at least a portion of the biocompatible membrane assembly is impregnated with a therapeutic agent.

48. The prosthetic valve of claim 1 wherein at least a portion of the biocompatible membrane assembly is impregnated with a pharmaceutic agent.

49. A prosthetic valve comprising:

a radially expandable structural frame including a proximal anchor and a distal anchor, the proximal and distal anchors being formed from a lattice of interconnected elements, and having a substantially cylindrical configurations with first and second open ends and a longitudinal axis extending there between;

one or more connecting members, the one or more connecting members having a first and a second end, the first end of each connecting member being attached to the proximal anchor and the second end of each connecting member being attached to the distal anchor; and a biocompatible valve assembly attached to the abluminal surface of the proximal anchor and extending distally along the one or more connecting members, the biocompatible valve assembly having proximal and distal ends, wherein the distal end is engaged with an abluminal surface of the one or more connecting members whereupon terminating with supple valve flaps biased towards an open position.

50. A prosthetic valve comprising:

a radially expandable structural frame including a proximal anchor and a distal anchor, the proximal and distal anchors being formed from a lattice of interconnected elements, and having a substantially cylindrical configurations with first and second open ends and a longitudinal axis extending there between;

one or more connecting members, the one or more connecting members having a first and a second end, the first end of each connecting member being attached to the proximal anchor and the second end of each connecting member being attached to the distal anchor;

a biocompatible valve assembly attached to the proximal anchor and extending distally along the one or more connecting members such that the distal end of the biocompatible valve assembly terminates in valve flaps that are slideably attached to an abluminal surface of at least one of the connecting members; and a stop integrated into the one or more connecting members to prevent sliding movement of the distal end of the biocompatible valve assembly past the stop.

* * * * *